(12) United States Patent
Klenerman et al.

(10) Patent No.: US 7,763,475 B2
(45) Date of Patent: Jul. 27, 2010

(54) MEASUREMENT AND USE OF MOLECULAR INTERACTIONS

(75) Inventors: David Klenerman, Cambridge (GB); Victor Petrovich Ostanin, Cambridge (GB); Fedor Nikolaievich Dultsev, Novosibirak (RU); Matthew Cooper, Cambridge (GB)

(73) Assignee: Inverness Medical Switzerland GmbH, Zug (CH)

( * ) Notice: Subject to any disclaimer, the term of this patent is extended or adjusted under 35 U.S.C. 154(b) by 531 days.

(21) Appl. No.: 11/706,654

(22) Filed: Feb. 13, 2007

(65) Prior Publication Data

US 2007/0218534 A1     Sep. 20, 2007

Related U.S. Application Data

(63) Continuation-in-part of application No. 10/350,892, filed on Jan. 24, 2003, now Pat. No. 7,195,909, which is a continuation of application No. 09/700,485, filed as application No. PCT/GB00/01587 on Apr. 25, 2000, now Pat. No. 6,589,727.

(30) Foreign Application Priority Data

Apr. 22, 1999  (GB) ................................ 9909308.0
Feb. 21, 2006  (GB) ................................ 0603392.2

(51) Int. Cl.
*G01N 33/551*  (2006.01)
*G01N 33/552*  (2006.01)

(52) U.S. Cl. ................. 436/524; 435/5; 435/6; 435/7.2; 435/7.32; 435/7.4; 436/527

(58) Field of Classification Search ........... None
See application file for complete search history.

(56) References Cited

U.S. PATENT DOCUMENTS 4,236,893 A    12/1980    Rice
4,242,096 A    12/1980    Oliveira et al.

(Continued)

FOREIGN PATENT DOCUMENTS

WO       WO 98/40739        9/1998

(Continued)

OTHER PUBLICATIONS

Karasek, F.W., "Cascade Particle Analyzer", *Chemical Abstracts*, 1979, abstract No. 11593, vol. 90, No. 2.

(Continued)

*Primary Examiner*—Christopher L Chin
(74) *Attorney, Agent, or Firm*—Saliwanchik, Lloyd & Saliwanchik

(57) ABSTRACT

The present invention is based on the realization that the bonds between a target molecule, or a target molecule attached to a particle, and a surface, can be ruptured by mechanically oscillating the surface at increasing amplitude, leading to detachment of the target molecule or particle from the surface. The required acceleration, and hence force, will depend on a variety of factors, including the mass of the molecule or particle, the nature of the bond to the surface and the geometric shape or size of the target molecule or particle. The present invention may therefore be used to separate or to size different target molecules, or to detect their presence.

20 Claims, 11 Drawing Sheets

U.S. PATENT DOCUMENTS

| | | | |
|---|---|---|---|
| 4,314,821 | A | 2/1982 | Rice |
| 4,735,906 | A | 4/1988 | Bastiaans |
| 4,999,284 | A | 3/1991 | Ward et al. |
| 5,501,986 | A | 3/1996 | Ward et al. |
| 5,552,274 | A | 9/1996 | Oyama et al. |
| 5,814,525 | A | 9/1998 | Renschler et al. |
| 6,086,821 | A | 7/2000 | Lee |
| 6,368,553 | B1 | 4/2002 | Lee |
| 6,630,309 | B2 | 10/2003 | Willner et al. |
| 6,764,860 | B2 | 7/2004 | Lee |

FOREIGN PATENT DOCUMENTS

| | | |
|---|---|---|
| WO | WO 98/45692 | 10/1998 |

OTHER PUBLICATIONS

Kolomenskii, Al. A. et al., "Interaction of Laser-Generated Surface Acoustic Pulses With Fine Particles: Surface Cleaning and Adhesion Studies", *Journal of Applied Physics*, 1998, pp. 2404-2410, vol. 84, No. 5.

Kösslinger, C. et al., "Comparison of the Determination of Affinity Constants with Surface Plasmon Resonance and Quartz Crystal Microbalance", *Eurosensors XII. Proceedings of the 12$^{th}$ European Conference on Solid-State Tranducers and the 9$^{th}$ UK Conference on Sensors and Their Applications, Proceedings of Eurosensors Conference*, Southampton, UK, Sep. 13-16, 1998, pp. 845-848, vol. 2.

Kurosawa, S. et al., "Latex Piezoelectric Immunoassay: Detection of Agglutination of Antibody-Bearing Latex Using a Piezoelectric Quartz Crystal", *Chemical and Pharmaceutical Bulletin*, 1990, pp. 1117-1120, vol, 38, No. 5.

Suleiman, A. A. et al., "Recent Developments in Piezoelectric Immunosensors", *Analyst*, 1994, pp. 2279-2282, vol. 119, No. 11.

Torres, L. et al., "A Quartz Crystal Microbalance to Determine Enthalpies of Sublimation at Intermediate Temperatures by the Knudsen Effusion Method", *Measurement Science and Technology*, 1994, pp. 51-54, vol. 5, No. 1.

Wang, A. W. et al., "A Silicon-Based Ultrasonic Immunoassay for Detection of Breast Cancer Antigens", *Sensors and Actuators*, 1998, pp. 13-21, vol. 49. Nos. 1-2.

Woodberry, M. E. et al., "Investigation of Accelerated Aging Characteristics of a SAW Filter", *Proc.-IEEE Ultrasonics Symposium*, 1997, pp. 55-60, vol. 1.

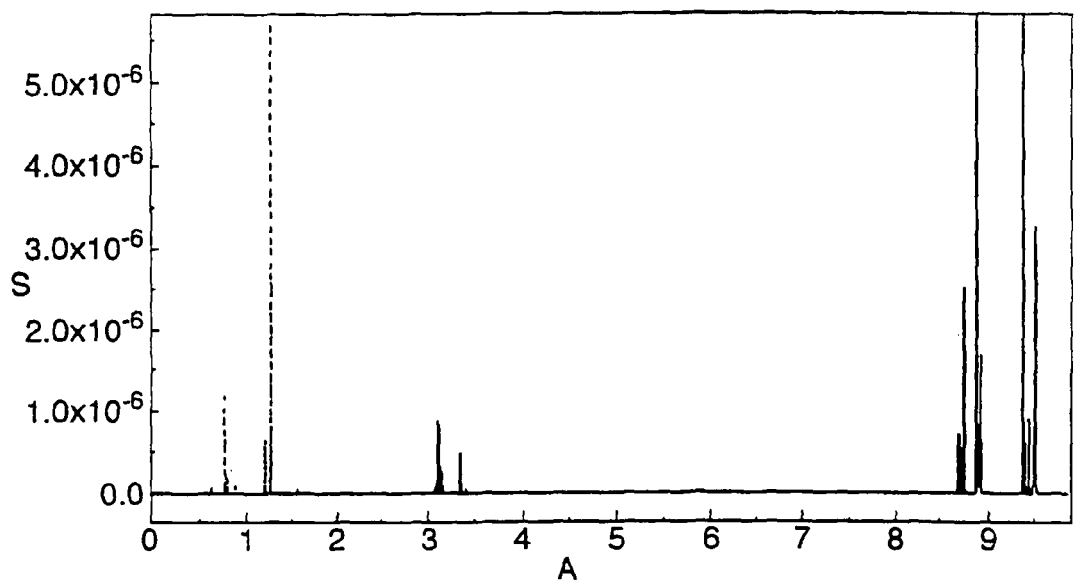
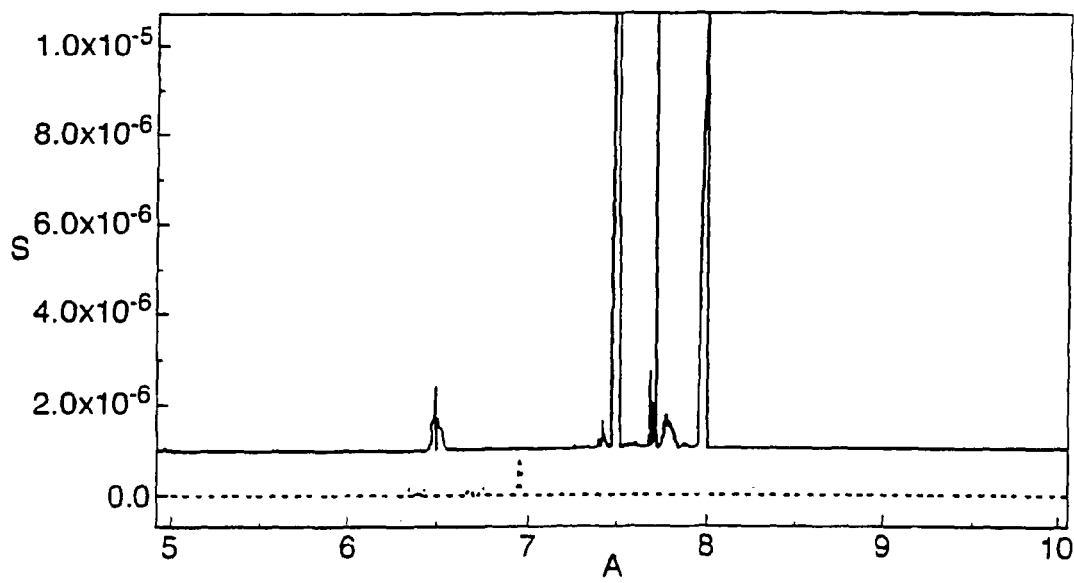

MEASUREMENT AND USE OF MOLECULAR INTERACTIONS

REFERENCE TO RELATED APPLICATIONS

This Application is a continuation-in-part of application Ser. No. 10/350,892, filed Jan. 24, 2003, now U.S. Pat. No. 7,195,909 which is a continuation of application Ser. No. 09/700,485, filed Nov. 15, 2000, now U.S. Pat. No. 6,589,727, which is a national stage application of PCT/GB00/01587, filed Apr. 25, 2000. It claims the benefit of priority from British Patent Applications Nos. 9909308, filed Apr. 22, 1999, and 0603392.2, filed Feb. 21, 2006.

FIELD OF THE INVENTION

This invention relates to methods for measuring molecular interactions and for separating, sorting and sizing particles.

BACKGROUND TO THE INVENTION

Specific molecular recognition is a fundamental process, being the basis of enzyme-ligand interactions, antibody-antigen interactions and the binding of molecules to receptors. Molecular recognition is achieved through non-covalent interactions such as electrostatic interaction (hydrogen bonds) and hydrophobic interactions. Thermodynamic measurements of binding constants and free energy, enthalpy and entropy changes offer insight into the molecular basis of recognition, particularly when coupled with information from X-ray diffraction and, when possible, site-directed mutagenesis.

Direct measurement of the force of interaction has been made by atomic force microscopy (AFM) as well as surface force apparatus. While AFM is capable of measuring bond rupture forces, the technique has the disadvantage that only one measurement can be made at a time. To date, AFM has been used on avidin-biotin interactions (Florin et al., Science, 1995; 264:415), DNA hybridisation (Boland et al, PNAS, 1995; 92:5291), antibody-antigen interactions (Dammer et al, Biophys. J., 1996; 70:2437) and adhesion glycoproteins (Dammer et al, Science, 1995; 267:1173).

Separating biological molecules on the basis of their relative affinities for ligands is a well recognised technique. For example, in affinity chromatography, the components to be separated are passed down a column that contains a specific ligand. The component of interest binds preferentially and strongly to the column and is retained on the column while the other components are removed. The bound material may be eluted off the column at a later stage.

Separation technologies are an important part of many research experiments. Increasing the sensitivity or selectivity of these techniques is desirable.

Kolomenskii et al, J. Appl. Phys., 1998; 84(4):2404-10, discloses surface cleaning and adhesion studies conducted using laser-generated surface acoustic pulses. The pulses were at a low repetition rate (20 Hz) and constant energy. The procedure was conducted in vacuum, and therefore is not suitable for commercial exploitation. An optical microscope was used to detect the removal of particles and it was not possible to distinguish between particles of different size.

WO98/45692 discloses the use of a piezoelectric crystal sensor for determining the formation/dissociation of clathrate hydrates. Kurosawa et al, Chem. Pharm. Bull, 1990; 38(5):1117-20, reports using such a sensor for the detection of agglutination of antibody-bearing latex. WO98/40739 also discloses such a sensor, including a plate on which specific binding entities are immobilised, for use in indicating the presence of cells in a medium. These sensors are used by measuring a change in resonance frequency at constant voltage.

At present, where possible, most viruses are detected by culture of the specimen in cells, since this method is sensitive although time-consuming. Direct detection of viral DNA or RNA in clinical samples can be achieved using PCR and specific primers tailored for the virus of interest. Since PCR involves an amplification step, cross-contamination is a major problem and it is difficult to establish reliable quantitative methods. Other direct methods include electron microscopy, immune electron microscopy, and methods based on antigen detection with enzyme-linked antibodies. These methods are often relatively insensitive and hence require relatively large quantities of the viral particles.

Many biotechnological processes are based on specific properties, such as the binding affinities, of one or more biological or chemical entities. For example, separation techniques may aim to separate one or more different entities having specific properties from a sample. A biosensor or analytical method may aim to detect only chemical or biological entities having specific properties, which may be present in a sample.

In such processes, it is often important to discriminate between entities with similar properties. For example, a separation technique, such as affinity chromatography, or a biosensor, may need to discriminate between similar entities with only subtle differences therebetween. Examples of properties which can be used to discriminate between biological or chemical entities include their size, mass, isoelectric point, presence or absence of labels, composition, structure, or the presence of recognition sites to which specific binding means can bind.

Biotechnological processes can be made to be specific by including process steps that use binding means with specific affinity for biological or chemical entities. Example binding means include antibodies or antibody fragments, chemical ligands, or nucleic acid sequences which have affinity for chemical and biological entities including specific recognition sites to which binding means bind. For example, antibodies or antibody fragments bind to regions of their ligands referred to as epitopes.

Processes which are capable of discriminating between chemically similar entities on the basis of their aggregation are useful in fields including biochemistry, biotechnology, microbiology, polymer-science and materials science.

Chemical or biological entities which are similar to each other in many ways but which have different recognition sites can be discriminated between if binding means with different affinities for the different recognition sites can be found. However, it is not possible to discriminate between entities in this way if they have only similar or identical recognition sites, or if binding means able to discriminate with sufficient specificity between two similar entities cannot be found or are not commercially viable.

Thus, antibodies and other binding means for binding specific recognition sites often cannot discriminate between an entity that is present as an unaggregated single component and an entity that is present in the form of an aggregate of a plurality of components. This is because the component may have the same or similar binding properties (such as presenting the same or similar recognition sites to specific binding means) whether or not it is aggregated.

There is a great deal of interest in detecting diseases of the brain, in animals or humans in which proteins form aggregates within cells in afflicted individuals. For example, Alzheimer's Disease is characterised by the formation of aggregates of β-amyloid peptide. Such aggregates typically comprise proteins which have a normal, non-disease state form present in the cells of the central nervous system as discrete non-aggregated monomers, and also a disease-state form in which they can aggregate. The disease and non-disease state forms may differ only in terms of configuration, and/or may have chemical differences. It is therefore desirable to determine whether such proteins are present in aggregated or discrete non-aggregated (monomer) form. A discrete protein and an aggregate of many proteins will both have similar properties and the same, or similar, epitopes to which antibodies and other binding means can bind, and so are hard to discriminate between by virtue only of the affinity with which they are bound by antibodies.

Some diseases in which proteins form aggregates in the cells of sufferers are believed to be transmitted by proteinaceous infectious particles referred to as prions which are typically modified forms of mammalian proteins. It is desirable to detect these protein aggregates and to enable the protein aggregates to be discriminated from unaggregated (or less aggregated) prion proteins, whether in their non-disease state form or modified disease-state form. In some diseases, the infectious particle is thought to be an aggregate of proteins and it is desirable to detect this infectious aggregate.

In some applications, an entity which is separated from a sample will be detected or measured. Immunological techniques, such as sandwich immunoassays, are known which can quantify the number of recognition sites present in a sample. However, they cannot in general discriminate between whether these recognition sites are present within an aggregate or whether those recognition sites are present on individual components.

Aggregates comprising a plurality of components could in principle be discriminated from unaggregated or less aggregated components by virtue of their different masses. However, conventional mass-sensing methods used in biotechnology, such as mass spectrometry, surface plasmon resonance detection, the use of field effect transistors, or enzyme-linked immunosorbent assays (ELISAs), cannot discriminate between, for example, a) one aggregate comprised of one hundred thousand monomer sub-units, and b) one hundred thousand discrete monomer sub-units. In general, both a) and b) will have identical or similar masses, and will present similar, or identical, recognition sites to binding partners in similar or identical numbers.

A potential causative agent of Alzheimer's Disease is the 4-4.5 kDa, 39-43 residue β-amyloid (βA4) peptide. This peptide is proteoytically cleaved from three larger proteins encoded by alternative splicing of the β-amyloid protein precursor gene (βAPP). βAPP proteins are usually O- and N-linked glycosylated transmembrane proteins of 695, 751 and 770 residues with a 47 residue cytoplasmic domain. βA4 corresponds to 28 extracellular residues and 15-16 transmembrane residues of the βAPP proteins. Proteolytic processing of βAPP proteins at a position equivalent to residue 16 of βA4 usually leads to shedding of the extracellular domain. However, an inappropriate cleavage event leads to generation of soluble, cytoplasmic βA4. Fibrillar aggregates of βA4 are formed when the protein is transformed by partial denaturing to the beta-sheet configuration, but only very slowly at physiological pH of 7-7.5. The aggregation process is more rapid at the lower pH of 5-6 (as found in some sub-cellular compartments), but also requires additional factors such as radical generation ormetal-catalysed oxidation systems. It is the aggregation of βA4 into fibrillar bundles that ultimately leads to neuronal cell death and the onset of dementia.

Accordingly, it is desirable to detect βA4 aggregates, perhaps in the presence of either or both discrete unaggregated βA4 or correctly processed βAPP proteins.

A potential causative agent of Parkinson's Disease is α-synuclein, a 14 kDa protein which in non-disease-state form is an intrinsically unstructured/unfolded presynaptic protein. However, when it is oxidised at tyrosine or methionine residues, it enters a partially folded, disease-state form which accelerates its polymerisation to form amyloid-like fibrils. In Parkinson's Disease, these fibrils lead to degeneration of dopaminergic neurons of the substantia nigra and Parkinsonia motor deficits. There is genetic evidence for a direct role of alpha-synuclein in early onset, familial Parkinson's Disease, including mutations (G209A) that enhance its stability and propensity to cause fibrils. Accordingly it is desirable to detect the formation of aggregated alpha-synuclein (in polymerised form), perhaps in the presence of discrete alpha-synuclein proteins (whether unoxidised or oxidised, normal or mutant).

A potential causative agent of neurodegenerative Huntington's disease is the ubiquitously expressed 55-60 kDa huntington protein. The huntington protein has little homology to other proteins, but in the disease state is characterised by amplification of a CAG codon in the open reading frame, leading to glutamine repeats in the mature protein. This polyglutamine region (comprising perhaps 80-100 glutamine repeats) in the full length protein leads to cytoplasmic aggregation, while smaller N-terminal poly-glutamine-rich fragments can form nuclear aggregations, resulting in neuronal death. It is therefore desirable to detect aggregates of the full-length protein or N-terminal fragments, perhaps in the presence of protein/protein fragments with fewer or no glutamine components.

In Creutzfeld-Jakob disease and Gerstmann-Straussler-Scheinker disease, the monomer prion protein exists in a ubiquitously-expressed, normal non-disease state cellular form ($PrP^c$), and a refolded, protease resistant, heat resistant, infectious disease-state form. For example, in the disease-state form of ovine transmissible spongiform encephalopathy neurodegenerative disease (scrapie) is referred to a $PrP^{Sc}$. $PrP^{Sc}$ is able to convert cellular $PrP^c$ to the infectious disease-state $PrP^{Sc}$ form. It is believed that the protease resistance of $PrP^{Sc}$ (and mutant form of $PrP^c$, e.g. P105L, D178N-129N, T183A, F198S) leads to the sequentration of the protein in inclusion bodies, where it self-assembles into beta-sheet oligomers, ultimately forming fibrils characteristic of the neurodegenerative Creutzfeld-Jakob Disease, Gerstmann-Sträussler-Scheinker Syndrome and fatal familial insomnia.

It is therefore desirable to detect aggregates of disease-state forms of $PrP^c$ and other prion proteins, perhaps in the presence of unaggregated disease-state or non-disease-state forms of $PrP^c$ and other prion proteins.

SUMMARY OF THE INVENTION

The present invention is based on the realisation that the bonds between a target molecule, or a target molecule attached to a particle, and a surface, can be ruptured by mechanically oscillating the surface at increasing amplitude, leading to detachment of the target molecule or particle from the surface. The required acceleration, and hence force, will depend on a variety of factors, including the mass of the molecule or particle, the nature of the bond to the surface and the geometric shape or size of the target molecule or particle. The present invention may therefore be used to separate or to size different target molecules, or to detect their presence.

According to one aspect of the present invention, a method for separating a target analyte from a composition, comprises the steps of:
(i) contacting the composition with a binding partner for the analyte, the binding partner being immobilised on a surface; and
(ii) oscillating the surface at increasing amplitude, to selectively remove the analyte, or other components of the composition, from the surface.

In addition, the present invention may be used in a method for determining the presence or size of particles, or the affinity between binding partners. According to another aspect of the invention, such a method comprises the steps of:
(i) contacting the binding partners, one of which is immobilised on a surface;
(ii) oscillating the surface at increasing amplitude; and
(iii) detecting a dissociation event.

In this aspect, the invention may be applied to a variety of physical and chemical bonds, ranging from relatively weak interactions such as hydrogen bonds through to covalent bonds.

A particular aim of this invention is to provide a method of separating an aggregate from a sample which can discriminate an aggregate from discrete components, or possibly aggregates of different sizes. In some embodiments, the presence or amount of aggregate may be determined.

The present invention aims also to detect or quantify the presence of aggregated components, perhaps in the presence of unaggregated discrete components.

The invention is therefore relevant to the detection of diseases such as Alzheimer's Disease, Parkinson's Disease, Huntington's Disease, Creutzfeld-Jakob Disease, new variant Creutzfeld-Jakob Disease, Gerstmann-Sträussler-Scheinker Disease, and fatal familial insomnia.

Apparatus suitable for use in the present invention comprises a surface having one binding partner immobilised thereon; means for oscillating the surface at increasing amplitude; and means for detecting a dissociation event.

In particular, the apparatus may comprise an acoustic transducer device (ATD), e.g. a quartz crystal microbalance (QCM) or surface acoustic wave device, or any piezoelectric material which can be made to oscillate, e.g. by applying an alternating voltage or magnetic field. These are cheap devices compared to an AFM and can be multiplexed. Another advantage of using such apparatus is that the majority of bonds are broken simultaneously, giving rise to detectable sound and sharp noise peaks at specific accelerations (applied voltage to the ATD). Another advantage is that the ATD can be used as a sensitive microphone, to detect the acoustic emission when the dissociation event occurs.

In most prior art experiments using an ATD, changes in the resonant frequency or phase have been measured when the ATD is driven at constant voltage. In contrast, the present invention involves increasing the driving voltage and hence the amplitude of oscillation of the ATD.

The present invention has widespread applications for separation, sorting and sizing. The Examples show that, in air, streptavidin-labelled spheres can be separated from normal latex spheres using a QCM with a biotinylated surface and with a driving voltage above 0.1 V but below 6 V. The normal latex spheres are removed from the surface, leaving only the streptavidin-labelled spheres attached to the surface (by the stronger streptavidin-biotin bond). This opens up a new form of separation science based on variable force applied for a certain length of time, with application, for instance, in particle-sizing and sorting, cell-sorting, panning for phage as well as the design of new biosensors. Such a separation method is of low cost and can easily be multiplexed and automated. For instance, it is possible to deposit different targets at different positions on the same microbalance and screen a library of ligands against multiple targets simultaneously. Detection and analysis of viral particles, which are of fixed size, is another area of application. Equally importantly, this invention provides a new, sensitive and potentially quantitative tool, to probe the forces involved in molecular recognition.

BRIEF DESCRIPTION OF THE DRAWINGS

FIGS. 4A-D show plots of signal noise (S; arbitrary units) versus amplitude (A; volts).

DESCRIPTION OF THE INVENTION

Figure 1:
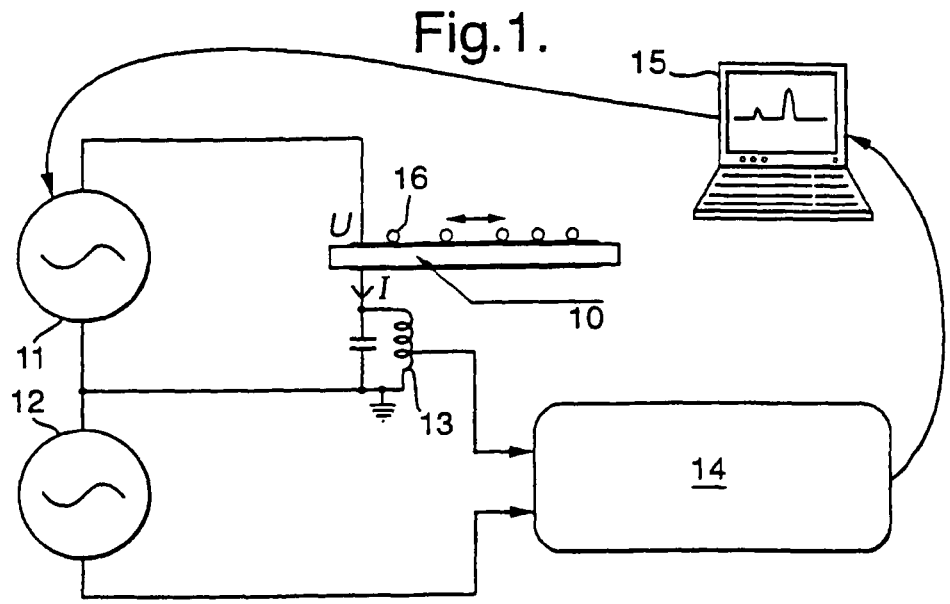
FIG. 1 shows a circuit comprising a piezoelectric transducer, a pure sinusoid f generator, a $3f+\Delta f$ generator, a $3f+\Delta f$ filter, a Lock-in amplifier and analog-to-digital converter, and a computer having a data input and a control output shown by arrows.

In particular, this invention typically relates to the separation of aggregates or oligomers from a sample. The term "aggregate" or "oligomer" is used herein to mean a plurality of components (which may be the same, similar or different to each other) joined or linked together (by physical or chemical bonds or forces) to form a single unit. In accordance with the Applicants' understanding, an aggregate is the term predominantly used to describe an assembly of misfolded disease-forming proteins, whereas an oligomer is used more generally to describe an assembly of 2 or more (typically a relatively low number ~-<30) protein monomers having a non-disease forming conformation. The monomers in an oligomer may not necessarily be of the same chemical species.

In the context of this invention, the term "aggregate" includes normal non-disease forming proteins; i.e. oligomers formed from proteins that are not misfolded in a disease-forming sense (although the monomeric units in the oligomer may have a different conformational state to that of the monomers).

The invention can be used to separate an aggregate or oligomer of monomers from the monomer itself. The monomer may be a protein. An aggregate may be of disease-forming proteins; an oligomer may be of non-disease-forming proteins. It will be understood that, when the aggregate is a prion, the protein constituent may be a misfolded or modified variant of the material protein.

The present invention makes use of sensor apparatus that can be made to oscillate. The sensor can be made to oscillate in a number of ways, e.g. by the use of surface acoustic wave devices, resonance quartz crystal devices, acoustic plate mode and thin membrane flexural plate devices.

Many different sensors, suitable for use in the invention, are available from commercial sources. A description of sensors that may be used in the present invention is contained in Acoustic Wave Sensors, Ballantine et al., (1997) Academic Press. The sensor is preferably a surface acoustic wave device, or, more preferably, a quartz crystal microbalance (QCM).

The QCM is typically a disc of crystalline quartz with gold electrodes on the top and lower surfaces. It undergoes a shearing oscillation when an alternating voltage is applied to the electrodes, due to the converse piezo-electric effect. Increasing the voltage increases the amplitude of oscillation of the QCM.

The quartz crystal is also a sensitive microphone and can be used to detect acoustic emission due to the rupture event. It is technically easier to excite oscillations at a frequency corresponding to one major resonance frequency, and detecting acoustic emission near to another mode. As an example, the QCM is driven at its resonance frequency, and the acoustic emission is detected at its third harmonic.

For the purpose of illustration, the term "analyte" may be used to describe the binding partner or component that is contacted with the surface-immobilised binding partner. Following contact, the analyte is bound to the sensor via molecular interaction and subjected to acceleration and hence a force is exerted on the analyte. As the amplitude of oscillation increases, and at a particular threshold force, bond rupture occurs. A previously bound analyte particle is thus free to roll on the surface.

The analyte may be any microscopic entity that is capable of being retained on the sensor via a molecular interaction. The analyte may be a protein, antibody, antigen, enzyme, enzyme inhibitor or polynucleotide. The analyte may also be a larger particle, such as a bacterium, cell, virus, prion or phage. Further examples of particles that are particularly suited for use in the present invention include microspheres of any material, e.g. silica, gold or latex, or large macromolecules such as plasmids. The surface-immobilised binding partner may be of the same type, and may be chosen accordingly, and depending on the appropriate physical or chemical bond.

The dissociation of smaller analytes is preferably detected by acoustic emission. Larger particles may also be detected by optical means, e.g. microscopy.

In one aspect of the invention, separation is carried out by immobilising the target molecule to a sensor surface via an interaction with a binding partner. The surface may then be oscillated to disrupt the molecules on the surface of the sensor. Oscillation is carried out by steadily increasing amplitude and therefore acceleration, and may be selected either to remove the target molecule from the surface, or to remove other components of the composition from the surface, leaving the target molecule bound to the surface. In a preferred embodiment, the sensor surface is oscillated by using a piezo-electric acoustic wave device, e.g. a QCM. The same piezo-electric device may be used as a microphone to detect acoustic noise produced by a rupture event.

The separation technique may be applied to select for molecules that interact strongly with a particular binding partner. For example, the technique may be applied to select cells with particular receptor molecules expressed at the cell surface, or to select for antibodies with strong affinity for a particular ligand.

Different ligands may be localised at different positions on the surface by, for example, contact printing or the use of masks or photolithography. It is then possible to screen a mixture for several strongly binding partners with several different ligands simultaneously. In particular, the invention can be used with chips having different materials such as receptors immobilised thereon. More generally, the chips can display materials that allow testing for different infections, pathogens, prions, food allergens, viruses, bacteria etc, e.g. in human and animal clinical testing, and for hygiene monitoring in food and water. Further, the invention can be used for library screening, phage display etc.

Another aspect of the present invention is a method for determining the presence or size of particles, or the affinity levels between molecules. Preferably, one molecule is immobilised to a sensor surface and the other is immobilised to a particle, e.g. a microsphere. The particle is then attached to the sensor via the molecular interaction of interest. The functionalised particles are then oscillated by applying a voltage to the sensor. As the amplitude of oscillation increases, the force reaches a critical value where bond rupture occurs. At this point, a characteristic noise may be detected by using a sensitive amplifier and the motion of the particles may be observed, e.g. under an optical microscope. The size of the signal depends on the number of particles bound to the sensor surface. Typically, if the QCM is used as described below, in Example 1, with physisorbed microspheres, noise is detected at 0.1-1V, dependent on the size of the microspheres, the onset occurring when the microspheres are observed to be sliding and escaping away, under the microscope. A plot may be made of noise generated versus amplitude (or applied voltage), which will be referred to as a rupture force spectrum. The point at which the bond ruptures will be apparent from the plot, as there will be a noise peak. Therefore, the critical voltage at which bond rupture occurs can be determined. Suitable calibration experiments, using particles having known bond densities and strengths, allow this method to be made quantitative. Further, the height of the acoustic emission peak is a measure of the number of bound particles.

The present invention may be used to study any molecular interaction, but is particularly suitable for the study of enzyme/ligand interactions, antibody/antigen interactions and receptor/ligand interactions or an interaction between a large macromolecule and its natural binding partner. The method may also be applied to the study of hybridisation events between polynucleotides. Thus, in the first aspect of the invention, the ligand may be, for example, a protein, an antibody or antigen, an enzyme, an enzyme inhibitor, a polynucleotide or a large macromolecule such as a large plasmid or virus. Either material may be bound to the surface or particle, in the second aspect of the invention. Preferably, and particularly in the context of separation, e.g. of aggregates, the properties of the system which are selected are properties of the oscillation of the surface. More preferably, it is the peak surface acceleration of the surface which is selected. The peak surface acceleration may be selected by determining the amplitude of the oscillations, the frequency of the oscillations and/or the waveform of the oscillations. Most preferably, the peak surface acceleration is selected by determining the amplitude of the oscillations.

The properties of the system which are selected may be set initially to individual values, or values within appropriate ranges, which enable discrimination of aggregate and discrete components (or less aggregated components). The properties may also be changed to individual values or values within an appropriate range which enable discrimination of aggregate and discrete components (or less aggregated components). These approaches are particularly applicable where the aggregate and components which may be present in the sample are known in advance, and corresponding values or ranges have been previously established e.g. by experiment.

The properties of the system may be changed with time to give a multistep process to reach conditions which enable discrimination of aggregate and discrete for less aggregated components. In particular, the properties of the oscillation of the surface may be changed with time. Changing the properties with time is particularly useful if the aggregate and components which may be present (and hence discriminating conditions) are not known in advance. Preferably the presence or absence of aggregate on the surface is monitored, directly or indirectly, while the properties are changed across a range of values (for example, the peak surface acceleration may be gradually increased). This enables detection and perhaps identification and/or quantification of the material present on the surface, and may also enable the properties or range of properties which allow discrimination between aggregate and discrete (or less aggregated components) to be determined.

In one embodiment, the sample is brought into contact with the surface while the surface is not oscillating, or is oscillating with properties (such as a sufficiently low peak surface acceleration) which allow an aggregate to bind or form thereon. Any discrete components present which can also bind to the binding means will also typically bind to the surface too. The surface is then oscillated with properties (such as a sufficiently high peak surface acceleration) appropriate to cause an aggregate of units to detach from the surface, but which allows discrete components to remain attached to the surface, thus separating the aggregate from any discrete components or, possibly, smaller aggregates which may be present.

Alternatively, the sample may be introduced in a fluid to the surface whilst the surface is already oscillating with properties (such as a sufficiently high peak surface acceleration) selected to prevent an aggregate of units from binding or forming thereon, but which allows other components that may be present, for example, discrete components or smaller aggregates, to bind to the binding means, thus separating the aggregate from any discrete components or, possibly, smaller aggregates which may be present.

The sample may also be introduced in a fluid to the surface whilst the surface is already oscillating with properties (such as a sufficiently high peak surface acceleration) selected to prevent not just an aggregate from binding or forming thereon, but also other components that may be present, for example, discrete components or smaller aggregates. The properties of the oscillation can then be changed (perhaps by reducing the peak surface acceleration) to allow the discrete components or, possibly, smaller aggregates to bind to the surface, but preventing the aggregate from binding to the surface. Accordingly, the aggregate is therefore separated from any discrete components or possibly smaller aggregates which may be present.

Where the properties of the system (particularly properties of the oscillation of the surface) are changed during the method, one or more properties may be changed gradually, or in one or more discrete step changes. Typically, the property of the oscillation of the surface which is changed is the peak acceleration of the surface. The peak acceleration of the surface depends on both the frequency and amplitude of the oscillation, and so an increase in the frequency or amplitude of oscillation will increase the peak surface acceleration, whereas a reduction in frequency and/or amplitude will result in a reduction in peak surface acceleration. Preferably, it is the acceleration which is varied.

A variety of mechanical oscillation modes can be used to generate accelerations on the surface of piezo-electric crystals, depending on their structure and cut. Amongst those suitable are surface acoustic wave, bulk acoustic wave mode and, preferably, transverse shear modes.

Typically, the method is carried out in the presence of a fluid, such as a liquid or gas. The fluid may be the sample, or a fluid derived from the sample, or another fluid. Aggregate which does not bind to the surface or which detaches from the surface will therefore be in the fluid. The fluid, including any aggregate present, may be removed for storage or analysis. In embodiments where aggregate is initially allowed to bind to the surface, the surface may then be washed by bringing a further fluid into contact with the surface. The surface may be washed before, after, or during oscillation of the surface by bringing a further fluid into contact with the surface.

A particular benefit is that the method can discriminate between an aggregate and discrete components or smaller aggregates even when the discrete or less aggregated components are present in the same sample in great excess. Discrete components, or smaller aggregates will become or remain bound to the binding means. Thus, an aggregate of components can be separated from a sample including an excess of discrete or less aggregated components.

Material remaining on the surface after oscillation (such as discrete components or smaller aggregates) can be removed by subsequently altering the properties of the oscillation appropriately (for example by increasing the peak acceleration of the surface).

The aggregate may comprise a plurality of identical or similar components. Unaggregated or less aggregated components may be identical or similar to the components which are comprised within the aggregate.

The method may involve a qualitative or quantitative detection step; for example, the step of detecting or measuring the amount of one or more analytes, preferably one or more constituents of the sample. Preferably, the analyte which is detected or measured is the aggregate.

The analyte that can be measured in situ on the surface, in the fluid, or after further processing of the fluid. The analyte may be determined after eluting it from the surface, preferably by increasing the peak acceleration of the oscillations of the surface.

Analyte present in the fluid can be detected by any known assay technique for determining the presence or amount of an analyte in a fluid, for example, optical absorbence techniques, fluorescence detection, chemiluminescence detection, direct or indirect (radio) ligand binding, western blotting, direct or indirect (radio or enzyme-linked) immunoassay, direct or mediated electrochemical detection.

Analyte which remains on the surface, may be detected by any known technique for determining the presence or amount of an analyte in a fluid, for example, by a direct or indirect radio or enzyme-linked immunoassay, direct or indirect (radio) ligand binding, direct or mediated electrochemical detection, quartz crystal resonance spectroscopy, measurement of optical absorbance, fluorescence or luminescence, surface plasmon resonance.

Analyte may be detected or measured by detecting or measuring the induced motional oscillation of the crystal generated whilst the surface is oscillated in a controlled way. As described above, acoustic energy is generated in a piezoelectric crystal when particles are dissociated from an oscillating surface, and the bonds between binding means and the particles are ruptured. Preferably, the properties of the oscillation of the surface are changed gradually and the induced motional oscillation generated by the rupture event is monitored whilst the properties of the oscillation of the surface are changing. Most preferably, the amplitude of the controlled oscillation of the surface is increased, whilst the frequency of the oscillations is held constant or approximately constant.

Oscillations of the crystal due to acoustic energy can be detected by measuring the potential difference produced at relevant frequencies. This might be achieved using a spectrum analyser, which can monitor multiple frequency channels simultaneously, and record signal information. Alternatively, a suitable frequency band may be monitored using a high extinction filter to pass only that frequency. Preferably, however, a resonance frequency of the crystal is used as the detection frequency.

Where the aggregate is present in a sample containing significant or substantial amounts of other materials, for example, discrete components, the process may be repeated to repetitively concentrate the aggregate. This may be achieved by removing the fluid containing the aggregate from the surface, and applying it to a fresh surface which can be oscillated as before, or the same surface after it has been treated to remove any remaining bound components, and the process can be repeated.

The method can also be used to concentrate aggregates from a sample, by bringing the sample into contact with the surface with the properties of the oscillation being such that aggregates can bind to the surface, and then removing the sample and replacing it with a lower volume of fluid before altering the properties of oscillation such as to dissociate aggregate from the surface into the lower volume of fluid. Sample may be applied in a fluid flowing across the surface. Aggregate may be collected from either a flowing or static fluid.

The surface may be the surface of a transducer, such as a piezoelectric transducer. Example piezoelectric transducers include a single crystal device such as those comprising quartz, lithium niobate, or zinc oxide; or piezoceramic devices, including integrated and retractable piezoceramic transducers. Piezoelectric polymers, such as polyvinylidene fluoride may also be used. The surface may also be oscillated using magnetostriction techniques such as magneto-acoustic resonance spectroscopy, electromagnetic techniques using a high magnetic field for the surface interaction, optical techniques, perhaps using a laser transducer, electronic techniques such as silicon micro-electromechanical devices or by remote action on a surface by an acoustic or ultrasonic transducer via an intermediate medium (e.g. a liquid, air, polymer, membrane, etc.).

Binding means may have affinity for specific recognition sites on the components and the aggregate. Suitable binding means for use with the present invention therefore include antibodies, antibody fragments, specifically binding chemical ligands, molecular imprinted polymers, and other means for forming a specific interaction with a component, or aggregate.

The binding means may be attached directly to the surface, or through an anchor layer, to provide good adhesion. For example, by the use of self-assembled monolayers, siloxanes, bilipid membranes, or immobilised (e.g. physisorbed) Protein A/G.

Importantly, the invention may be used to separate, and optionally detect or measure aggregate, even when the components from which the aggregate is made are too small to be detected themselves, for example, by the rupture event sensing approach described above.

The invention finds particular application in the detection of aggregates of disease-state proteins, such as are found in many neurodegenerative diseases including Alzheimer's Disease, Parkinson's Disease, Huntington's Disease, Creutzfeldt-Jakob Disease, new variant Creutzfeldt Jakob Disease, Gerstmann-Sträussler-Scheinker Disease and fatal familial insomnia. For example, aggregates of disease-state amyloid b protein are found in Alzheimer's disease patients. It may be desirable to separate these aggregates from discrete proteins, such as unaggregated disease-state or non-disease state proteins, for example, in diagnostic tests.

Thus, the method may be used to detect the aggregates found in vivo in neurodegenerative diseases, including prion dieases.

Importantly, the method can be used to separate or determine the presence or amount of these aggregates even in the presence of a great excess of discrete monomers. For example, aggregates of $PrP^{Sc}$ may be determined in the presence of excess $PrP^{C}$ and/or excess unaggregated $PrP^{Sc}$. Thus, the method can be used to detect neurodegenerative diseases associated with protein aggregate formation, at a very early stage, even when only a very low proportion of the component proteins are present in the form of aggregates in a cellular or body fluid.

Typically, aggregate will be detected in cerebrospinal fluid, or other bodily fluids such as blood (e.g. blood for transfusion) or urine. Aggregate might also be detected in lymphoid tissues such as the tonsils or spleen.

Examples of aggregates include those which comprise components held together by non-covalent binding and other forces such as hydrophobic binding and Van der Waals forces. The invention is also applicable to aggregates including covalent bonds between components.

The monomers which constitute the components from which aggregates are formed, may be the same or different to normal, discrete non-disease-state proteins. Some disease-state prions are believed to be chemically identical to non-disease-state prion proteins, except that they exist in a different 3-dimensional structural configuration. For example, infective protein PrP$^{Sc}$ contains a higher percentage of the beta-sheet folded structure than normal PrP$^c$, which contains a higher percentage alpha-helical structure. Disease-state proteins which form aggregates may also differ from non-disease-state monomer proteins by virtue of having different chemical compositions, for example, inserted or deleted peptide units (e.g. the point mutations of PrP$^c$: P105L, D178N-129M, T183A and F198S).

Figure 11:
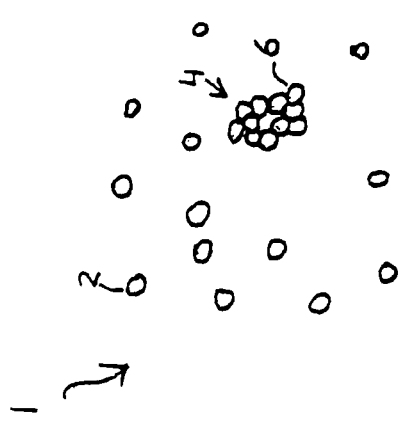
FIG. 11 illustrates schematically a sample including an aggregate.

FIG. 11 illustrates a sample 1 isolated from nerve cells, in the form of a liquid including both discrete non-disease state proteins 2, and an aggregate 4 comprised of disease-state proteins 6 which have formed into an aggregate.

Figure 12:
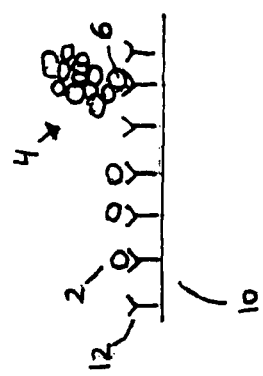
FIG. 12 illustrates the sample of FIG. 1 brought into contact with a surface which is not oscillating.

FIG. 12 illustrates the introduction of a sample 1 to a quartz crystal surface 10 having antibodies 12, functioning as binding means, immobilised thereon, whilst the surface 10 is not oscillating. Both discrete proteins 2 (where present) and aggregates 4 (where present) bind to the binding means 12, by virtue of the specific bond formed between the antibodies 12 and epitopes on the discrete proteins 2 or aggregated proteins 6. The surface is then washed to remove any unbound materials.

Figure 13:
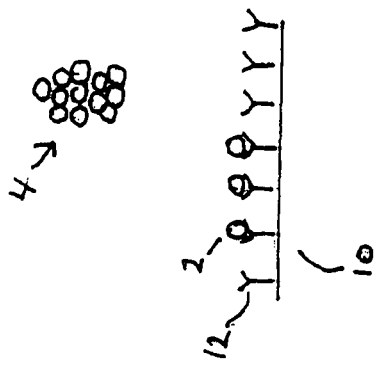
FIG. 13 illustrates the results of oscillating the surface shown in FIG. 12 with properties so as to dissociate the aggregate.

Next, the surface is brought into contact with a liquid and oscillated with a frequency and amplitude which result in a peak surface acceleration sufficiently high to cause the aggregate 4 to dissociate from the surface, into the liquid where it can be collected, leaving behind discrete proteins 2 which remain attached to the oscillating surface 10, as shown in FIG. 13. Accordingly, aggregate 4 has been separated from discrete proteins 2.

The liquid in contact with the surface, including the aggregate 4, is then removed where it may be stored for use, or an assay may be carried out in order to determine the presence and/or amount of aggregate therein. Appropriate assays, for example, optical absorbance assays, fluorescence assays, chemiluminescence assays, direct or indirect (radio) ligand binding, western blotting, direct or indirect (radio or enzyme-linked) immunoassays, direct or mediated electrochemical detections etc, are well known to those skilled in the art.

Estimates can be made of the force applied to biological particles under such conditions.

The acceleration of a particle attached to the surface of a crystal oscillating at 14.2 Mhz, and driven at a typical detachment voltage of 7V, without accounting for viscous forces induced by the fluid, is ~$3 \times 10^7$ ms$^{-2}$. It is known that an aggregate of prions having $10^6$ monomers constitutes an infectious unit. Experimentally created prion rods having ~$10^3$ monomers have also been determined to show infective activity. A typical infectious unit might therefore contain approximately 100,000 PrP$^{SC}$ monomers, each with a mass of 35 kDa, giving an infectious unit mass of $3.5 \times 10^9$ Da, or ~200 fg. A simple mechanical calculation leads to an estimate of the forces applied to the aggregate as ~700 nN. In the most general case attachment at several points will occur. For a filament-like aggregate, where the antibody is capable of attaching to epitopes on individual monomers, a number of attachment points along the length of the aggregate can be anticipated, but this force will still be sufficient to cause detachment of the aggregate.

Figure 14:
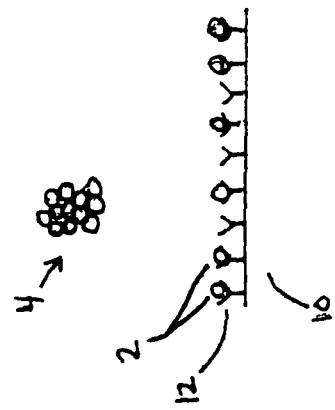
FIG. 14 illustrates the sample of FIG. 1 after bringing it into contact with an oscillating surface, wherein the properties of the oscillation of the surface are selected to allow discrete proteins to bind to the surface but not protein aggregates.

In a second example, shown in FIG. 14, the sample 1 is brought into contact with an oscillating surface of a quartz crystal 10, which has immobilised thereon a plurality of antibodies 12 which function as binding means and bind specifically to an epitope present on both non-disease-specific protein monomer 2 and disease-specific protein 6.

When the sample 1 is brought into contact with the surface 10, the surface is already oscillating in surface shear mode. The amplitude and frequency of the oscillations are set to give a peak surface acceleration sufficiently low to allow protein monomer 2 to bind to the antibodies 12. The surface shear motion of the transducer induces shear motion in the adjacent fluid layer, and the discrete protein monomers move under the influence of this motion relatively easily. However, the protein aggregate 6 has a higher mass and so moves with a lower amplitude than the surface, inhibiting the formation of bonds with the surface. However, the peak surface acceleration is sufficiently high to prevent the binding of protein aggregate 6 which, due to its mass, would need to be subject to greater forces between the antibodies 12 and disease-specific proteins 6 in order to move with the oscillations of the surface. Suitable conditions can be readily determined by experiment.

The liquid including the aggregate may be removed for storage, and/or analysis.

Any discrete proteins or aggregated proteins which remain on the surface may be measured, for example by using radio-labelled versions of monnomers, and detecting their presence on the surface by scintillation counting. Aggregates might also be detected using scanning electron miscroscopy. Protein is first fixated on the surface by the use of glutaraldehyde and osmium tetraoxide, then dehydrated and coated with gold. Examination by electron microscope can show up protein aggregates.

Quartz crystal oscillators can be prepared using a variety of standard crystals. Quartz crystals (AT cut, plano-plano, 8.2 mm diameter) from Morion (St Petersberg, Russian Federation) were coated on both sides with a 5 nm adhesion coat of chromium and a top layer of 65 nm of Gold by standard evaporation techniques. When coated the crystal had a fundamental resonant frequency of 14.2 MHz and a Q-factor of approximately 50,000. The coated crystal was mounted in a ceramic holder having a circular aperture with a lip on which the crystal sits and cemented in place using two points of conductive epoxy adhesive, which also provide electrical connect with tracks which are screen printed onto the holder. The crystal mounted in the holder is then located in a cell machined from PEEK (polyetherether ketone), where the active side of the crystal was sealed against an 0-ring, to provide a liquid tight seal. An aperture above the active surface of the crystal provided a static reservoir of 50 ml volume for sample analysis.

A number of means are available to drive the oscillator with a controlled amplitude, for example using a drive circuit with a phase locked loop. Those skilled in the art will recognise a large variety of ways in which this crystal driving can be done. In the direct drive method, a frequency synthesiser is used to generate a drive signal at a resonant frequency of the crystal. The drive signal is filtered to eliminate unwanted overtones, and applied to the crystal. A computer can be used to control the amplitude of the drive signal by controlling the gain of an amplifier. Detection of the energy released by the detachment of the aggregate is carried out by filtering the voltage across the crystal with a bandpass filter to remove the fundamental frequency and pass only the detection frequency. The rupture event signal may be detected in a band of frequencies around the third overtone, by mixing the output with a reference signal having three times the fundamental frequency. As the drive voltage is scanned this signal is sampled and converted to digital form for analysis. The detected signal as a function of applied drive voltage can then be examined to find peaks which indicate a detachment event.

The following Examples illustrate the invention.

In the Examples, rupture force spectroscopy is used to measure the adhesion forces between a surface and a small particle. This effect is based on oscillating a surface, with microparticles on it, at monotonously increasing amplitude and hence increasing acceleration. This is achieved by means of driving the surface with a piezoelectric acoustic wave device, in this case a quartz crystal microbalance (QCM). As the amplitude increases, so does the acceleration and hence the force exerted on the particle. The rupture of all the bonds attaching the particle to the surface results in acoustic noise and the same piezoelectric device is used as a sensitive microphone to detect this noise, produced by the rupture event. A schematic representation of the apparatus used in Examples 1 to 5 is shown in FIG. 1; a more general schematic representation of the preferred apparatus is shown in FIG. 8.

More specifically, FIG. 1 shows a circuit comprising a piezoelectric transducer 10, a pure sinusoid f generator 11, a 3f+Δf generator 12, a 3f+Δf filter 13, a Lock-in amplifier and analog-to-digital converter 14, and a computer 15 having a data input and a control output shown by the arrows. In Examples 1-5, f=14.2 MHz, and Δf is 82 kHz. Particles 16 are placed on the surface of the substrate.

Figure 8:
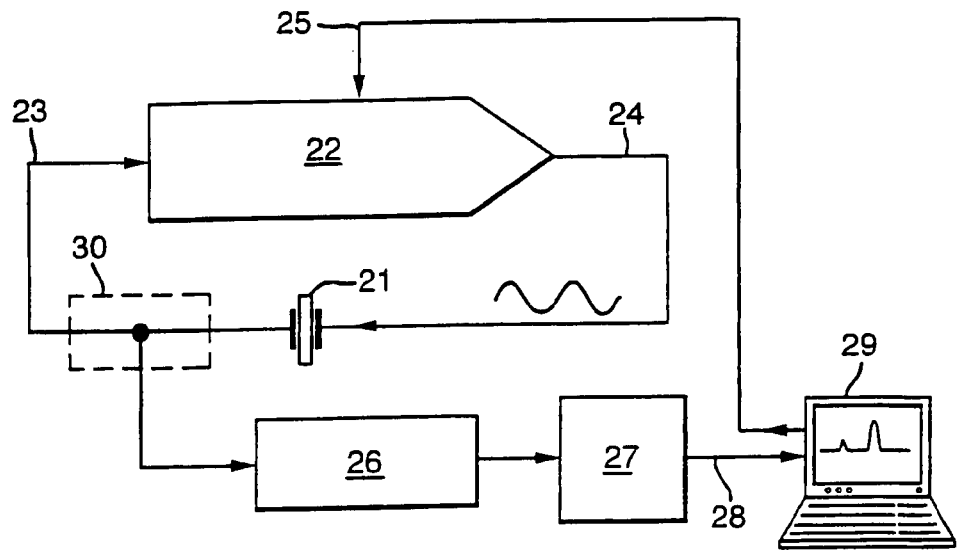
FIG. 8 shows a more general schematic representation of the preferred apparatus.

FIG. 8 shows a piezoelectric transducer 21 (such as QCM, SAW device, etc.), and a variable gain amplifier 22 with input 23 and output 24 capable of delivering smoothly rising output amplitude under control of a signal 25. The circuit also comprises a bandpass receiver 26 (for example similar to a SSB radio receiver), and an analog to digital converter or converters 27 supplying data via a link 28. Further, the circuit comprises a controller, recording and data signal processing device 29 (for example computer or specialised DSP processor). The contact indicated by a broken line 30 can be replaced by more optimised filtering and-coupling means, e.g., it may be a passive L, C, R network.

In use of the circuit shown in FIG. 8, the amplifier 22 with transducer 21, together with optional filtering/coupling means 30, provides a simple oscillator network, oscillating preferably at a frequency where the transducer is efficient; for QCM it may be a fundamental series resonance frequency. This oscillation frequency (F) is, e.g. 14 MHz. The amplitude of driving voltage at output 24 rises smoothly under the control of the controller 29 by means of the control link 25. The emerging signal of acoustic emission at point 30 may be purified by means of an optional filter/coupler and then fed to the input of the bandpass receiver 26. The working receiver frequency band may be selected by a maximum signal-to-noise criterion, e.g., the resonance mode located near to the third harmonic (3*F+ΔF), e.g. 42.082 MHz.

Single or quadrature output signals are converted by an analog to digital converter or converters 27 of high dynamic range. The data are then further digitally processed at 29, in order to extract useful signal, and then recorded and/or presented to the observer. The amplifier 22 may be additionally equipped with passive output and/or input filter(s), improving the signal to noise ratio, and also ensuring that the oscillator works under the correct frequency and phase shift of current to voltage across the transducer.

Figure 9:
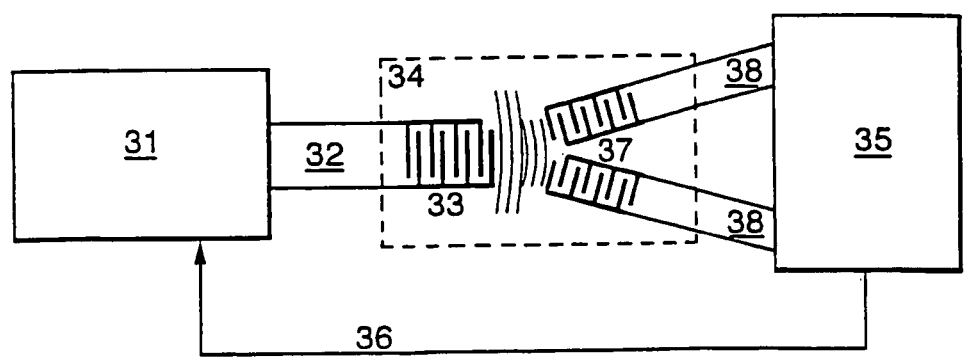
FIG. 9 shows a preferred SAW-based sensor for use in the present invention.
Figure 10:
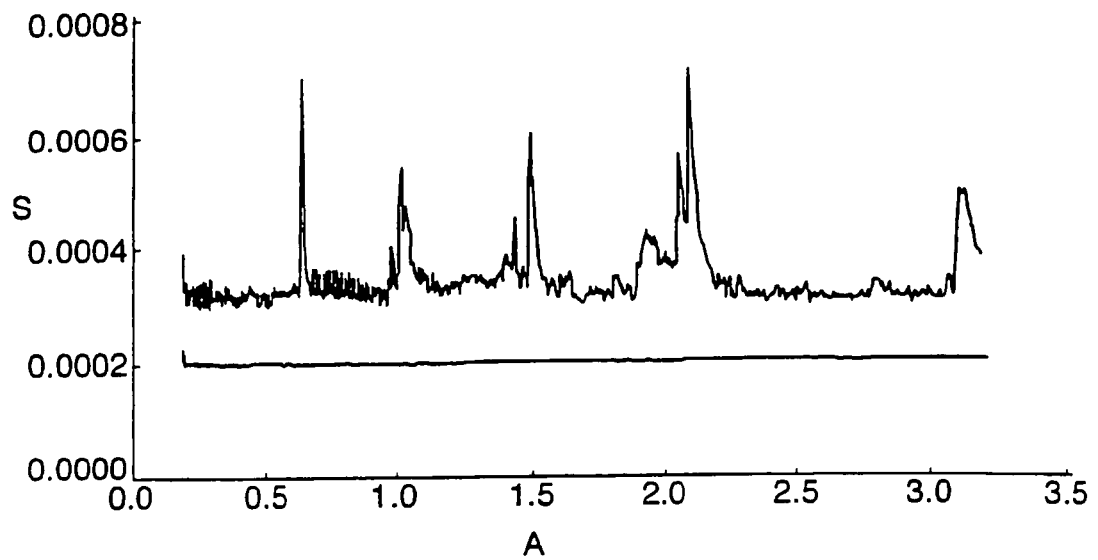
FIG. 10 shows plots of signal noise (S; arbitrary units) versus amplitude (A; volts).

FIG. 9 illustrates a preferred SAW-based sensor for use in the invention. It comprises means 31 for generating RF voltage at output 32 with increasing amplitude which drives transducer electrodes 33. The electrode arrangement 33 is optimised for the generation of high amplitude SAW at a piezo-substrate 34. The electrode arrangement 37 is optimised for best transduction of acoustic emission to an electrical signal. The pattern may be complex, comprising one or more pairs of electrodes. The device further comprises a control unit 35 for controlling the generator 31 by means of a link 36 and for receiving generated signals at one or more inputs 38 and performing data signal processing, e.g. correlation analysis.

In use of the SAW-based sensor, the generator 31 generates RF voltage that is suitable for providing an efficient transducing frequency at output 32, and this is fed to generating transducer electrodes 33 located on the piezo-substrate 34 (dotted line). The amplitude of RF voltage rises over time under the control of the controller 35 by means of the control link 36. The receiving electrodes 37 transduce the acoustic emission that emerges from the active area to an electrical signal which is fed to the receiver/controller 35 and input(s) 38. The data obtained after analog to digital conversion then undergo signal processing in order to extract useful signals. Results are then finally recorded and/or presented to operator.

Certain results from Examples 1 to 6 are shown in FIGS. 2 to 7 and 10. FIGS. 2A, 2B, 3A, 3B, 4A, 4B, 4C, 4D, 6B, 7 and 10 are plots of signal noise (S; arbitrary units) versus amplitude (A; volts). FIGS. 5A, 5B, 6A and 6C are plots of signal noise (S; arbitrary units) versus number of particles (N).

The following abbreviations are used:
BSA: Bovine serum albumin
LB: Luria broth
DIC: Dimethylaminoisopropyl chloride
DMAP: Dimethylaminopyridine
EDC: 1,3-dimethylaminopropyl-3-ethylcarbodiimide
NHS: N-hydroxysuccinimide
PBS: phosphate-buffered saline

EXAMPLE 1

Latex spheres, 5 μm in diameter, were attached to a QCM sensor surface via multiple numbers of the bond of interest. The coverage of the spheres used was 1% of the surface area of the QCM. The spheres had only 1% variation in their diameter.

The QCM sensor comprised polished quartz plates, acoustic traverse-cut at 35°, and 8.25 mm in diameter. Layers of chromium (20-30 nm thick) and then gold (100-120 nm thick) were deposited.

Three different bonds were studied, in experiments conducted in air: a physical bond (latex-gold), a streptavidin-biotin bond and a covalent bond (amide linkage). The physical bond was made by placing the latex spheres directly on the sensor surface and drying in nitrogen. The streptavidin-biotin bond was made by applying biotinylated BSA to the surface, and drying in nitrogen. The chemical bond was made by forming a thiol monolayer using an acid-terminated thiol (12-mercaptododecanoic acid) dissolved in ethanol; this was then activated using EDC-NHS, and the amine-terminated spheres were added to form the amide bond.

The experiments were performed in a chamber equipped with two optical windows: one to provide laser illumination of the sample, and the other to allow observation of the scattered laser light by an optical microscope. The QCM was placed in the chamber. A signal generator, Model DS345 (Stanford Research Systems), was used to drive the QCM. Motion and detachment of particles were observed using an Olympus BH-2 optical microscope equipped with a CCD Panasonic WL-SL300 video camera. The main measuring device was a Lock-in amplifier, SR 844 (Stanford Research Systems). The reference signal was fed to the Lock-in using a second generator synchronised to the first one. All devices were interfaced to a computer for control of the experiment and collection of the data.

Figure 2A:
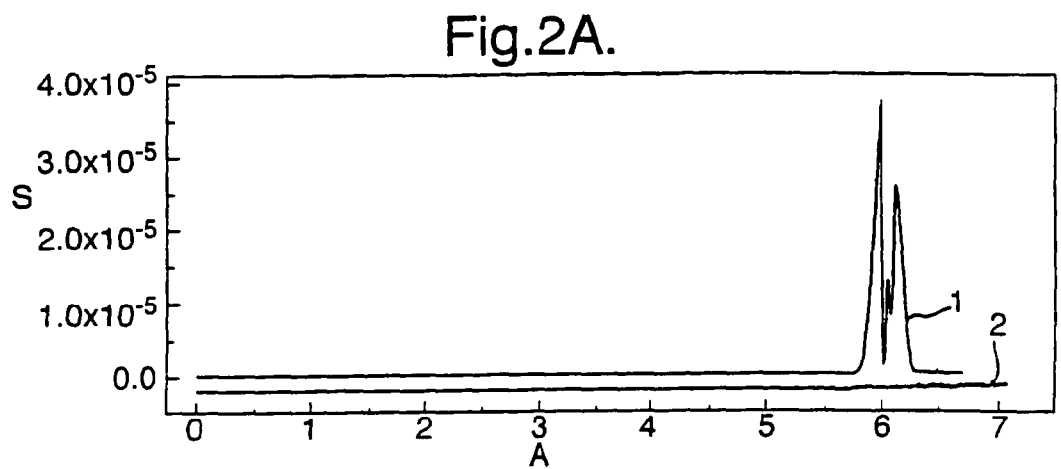
FIGS. 2A-B show plots of signal noise (S; arbitrary units) versus amplitutde (A; volts).
Figure 2B:
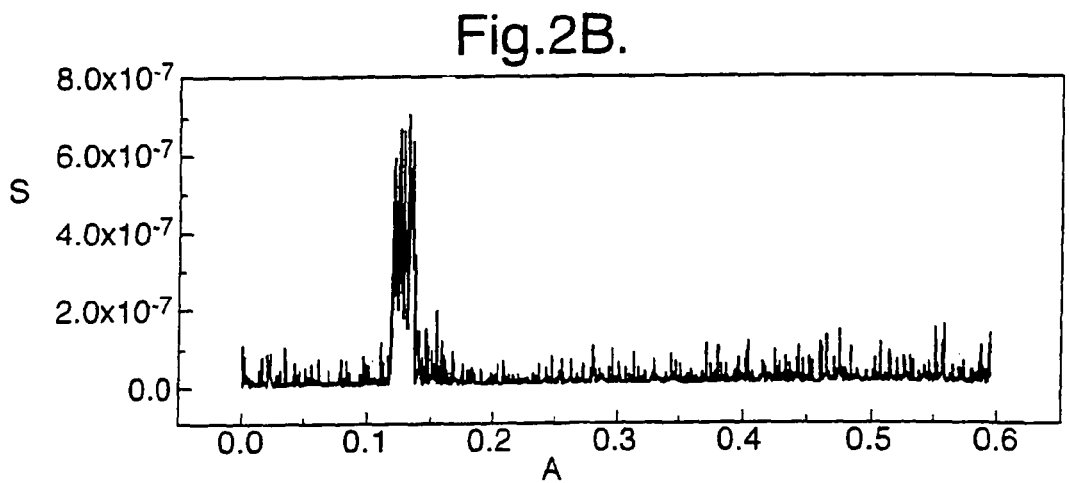

FIG. 2A shows the rupture force spectra for streptavidin-biotin (1) and the chemical bond (2); FIG. 2B is the spectrum for the physical bond.

By recording the rupture force spectra, it is possible to determine experimentally the force or voltage required to break the bonds. This can be used for separation. As shown in FIG. 2A, if there is a mixture of 5 µm spheres, some of which have streptavidin on the surface and some which do not, then by applying a voltage above 0.1 V but below 6 V, say 1 V, to a QCM with biotin on the surface, it is possible to separate the two sets of spheres to provide only streptavidin-labelled spheres on the surfaces. This technique may also be used to detect streptavidin-labelled spheres, since only these spheres would bind to the surface if oscillated at 1 V.

To make the measurement quantitative, the amplitude of oscillation of the QCM has been calculated at different voltages, based on experimental data, allowing estimation of the force on the microsphere. This estimate was performed by measuring the power consumption of the QCM and its Q factor (or merit factor–the reciprocal relative resonance bandwidth=$f/\Delta f_{resonance}$). The amplitude A is given by:

$$A=[QP/2\pi^3 f^3 M]^{1/2}$$

where Q is the Q or merit factor, P is the electrical power consumed by the QCM, f is the resonant frequency of the quartz crystal and M is the effective mass of the QCM quartz plate involved in motion. The Q factor was determined to be c.15000 at 6V, which gives an estimate of the vibrational amplitude of the QCM of 60 nm. The force on the sphere is therefore 9 µN. This should be compared to the force needed to break a single streptavidin-biotin bond of 160 $pN^2$ and indicates that approximately 60,000 bonds are broken simultaneously. Estimation indicates that this corresponds to 50% or more of the initial streptavidin-biotin bonds between the sphere and the surface. This means that the majority of the bonds attaching the spheres to the surface are broken simultaneously. This gives rise to the sharp peaks observed in the rupture force spectra and the detectable noise on bond breakage.

EXAMPLE 2

This Example shows that methods of the invention may also be carried out in solution. The Q factor of the QCM will decrease due to liquid loading, thus reducing the amplitude of oscillation at a particular voltage when compared to air. There will be viscous forces acting on the microsphere and its effective mass will increase, due to the associated layer of water, increasing the force on the sphere.

Figure 3A:
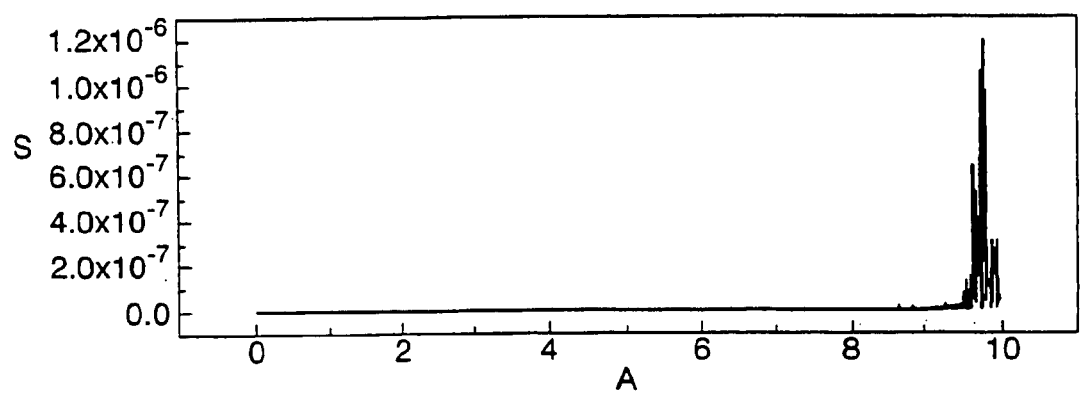
FIGS. 3A-B show plots of signal noise (S; arbitrary units) versus amplitude (A; volts).
Figure 3B:
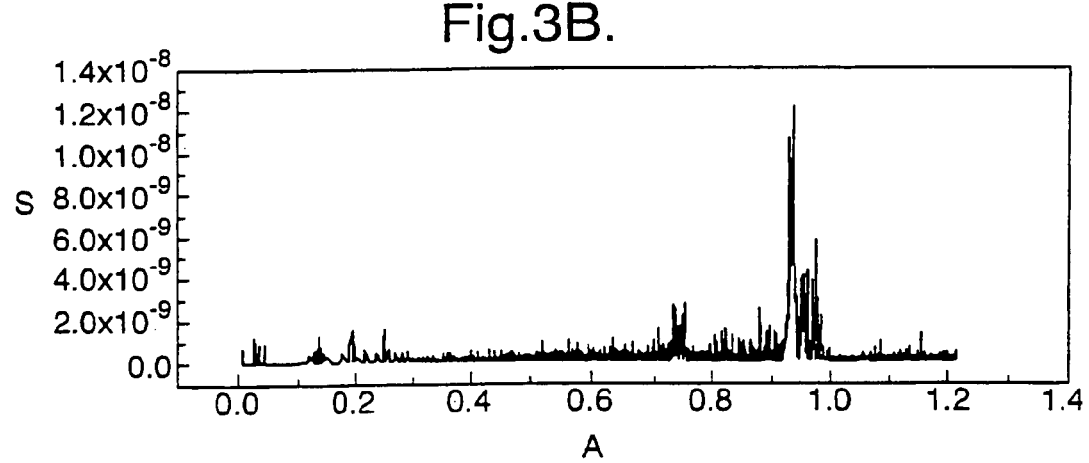

FIG. 3 shows the rupture force spectra for 5 µm latex spheres attached to the surface via streptavidin-biotin (FIG. 3A) and a chemical bond (FIG. 3B). Rupture occurs respectively at 1 V and 10 V.

A reduction in the critical voltage for the streptavidin-biotin bond, by a factor of six, from 6V to 1V on going from air to water, and the breakage of the chemical bond in water, indicates that the latter effect is dominant. Thus, this Example clearly demonstrates that bond-breaking, and hence separating and biosensing, are possible in water liquid or another.

Assuming that the bond density for the physical, streptavidin-biotin and chemical bonds is the same and since the same size microspheres have been used in these experiments, a relative scale of rupture force can be obtained. This is 1:60:600 for the physical:streptavidin-biotin:chemical bond. This scaling appears reasonable and demonstrates the dynamic range of this method. By conducting suitable calibration experiments with known bond densities, it should be possible to make these measurements quantitative.

EXAMPLE 3

The Example demonstrates the detection of viruses, and in particular genetically modified bacteriophage displaying a maltose-binding protein fused to the phage pIII coat protein, since both the phage and the maltose-binding interaction are well characterised and readily available. The phage is a long, thin, filamentous virus consisting of a flexible rod 1 µm long and 6 nm in diameter. The genetically modified phage additionally display up to 5 maltose-binding proteins at one end of the virus as fusions to the phage pIII coat protein; see McCafferty et al, Nature, 1990, 348:552. These phage can be specifically purified on amylose resin.

A maltose-binding protein fusion to the amino terminus of indole glycerol phosphate synthase was displayed on the surface of fd phage as a fusion to the amino terminus of the gene III-encoded coat protein. For this purpose, an fd phage vector, pJB113, was constructed; it encoded a genetic fusion between MalE (*E. coli*), trpC (*E. coli*) and gene III. This phage vector carried a tetracycline-resistance marker. The unmodified competitor phage was VCS M13 K07 helper phage (Stratagene) carrying a kanamycin-resistance marker.

Bacteriophage concentrations of $1\times10^{12}$ cfu/mL were obtained by infecting a 3 mL mid log phase LB culture of *Escherichia coli* strain TG1 with 10 µL of phage stock. After 2 hours of shaking (250 rpm) at 37° C., 1 mL of culture was inoculated into 100 ml LB and shaken at 350 rpm, 37° C. for 1 hour. Tetracycline (10 µg/mL) or kanamycin (50 µg/mL) was added to the pJB113 or VCS culture, respectively, which was grown overnight at 30° C., 250 rpm. Bacteria were pelleted (15 mins, 4.1 krpm) and the phage precipitated from the supernatant by addition of NaCl and PEG6000 to final concentrations of 0.5 M and 4% (v/v) respectively. After standing for 1 hour on ice, the phage were recovered by centrifugation (30 mins, 4.1 krpm) and the phage pellet was resuspended in 1 ml $H_2O$ and stored at 4° C.

Soluble starch (500 mg, 0.01 mmol, 1 eq.) was dissolved in DMF (10 ml) and stirred for 5 min (partially soluble). To 11-mercaptododecanoic acid (11.5 mg, 0.05 mmol, 5 eq.) in DMF (0.5 ml) was added DIC (7.8 µl, 6.3 mmol, 0.05 mmol, 5 eq.) and DMAP (cat.) and this solution was added to the starch solution. The reaction was left stirring at room temperature overnight. The reaction was then purified using a stirred cell with a 10000 MW membrane cut-off, by rinsing the solution with milliQ water (6 times 50 mL) and concentration, followed by lyophilisation overnight.

The surface was prepared using the modified starch containing a thiol group so that it could be chemically coupled to the surface. The QCM (prepared as in Example 1) was placed in a solution of the starch in methanol (1 µg per mL) for 12 hours. The samples were then washed and dried under a stream of nitrogen. The viruses were deposited on the surface from solution and dried at room temperature for experiments in air. Different virus concentrations were made by dilution. To perform the experiments with maltose blocking the maltose-binding protein, 100 nM maltose was added to the solution of phage.

The surface of the QCM was thus coated with a layer of soluble potato starch (which contains branched polymers of maltose), chemically attached to the gold surface via a sulphur-gold bond. Experiments were performed in both air and water.

FIG. 4A shows the rupture force spectrum obtained in water for an equal mixture of maltose-binding phage (–) and unmodified phage ( . . . ), the scan being acquired over 500 seconds. There are approximately 500 million of each type of phage on the surface of the gold electrode. For the unmodified and hence non-specifically bound phage, a rupture peak was detected at 1.2 V. The corresponding rupture peaks for the maltose-binding phage were around 9 V and are more intense than the non-specifically bound phage due to the greater energy released on bond breakage. In air, no peaks from the specifically bound maltose-binding phage were observed up to 10 V; FIG. 4B shows the data in air for just the non-specifically bound phage. The peak occurs at 7.5 V, an increase of approximately 6 over the peak found in water. A second scan ( . . . ) has almost no peaks, indicating that the phage have been removed from the surface. This confirms that the additional viscous friction forces and the increase in effective mass of the particle make it easier to rupture the bonds between the phage particles and the surface in water than in air.

The sharpness of the peaks in the rupture force spectrum is apparently linked to the observation that the bond rupture occurs at a threshold voltage; this results in the acoustic noise occurring in a short time period and hence makes the method very sensitive. In addition, the signal from the specific binding phage is well separated from the non-specific binding phage and at higher amplitude, which means that non-specific adsorption does not affect the measurement of specific adsorption. A much larger force is required to rupture the specific interaction between the maltose-binding proteins displayed on the phage and the starch-coated surface compared to that required to rupture the non-specific interactions between unmodified phage and the surface.

Figure 4C:
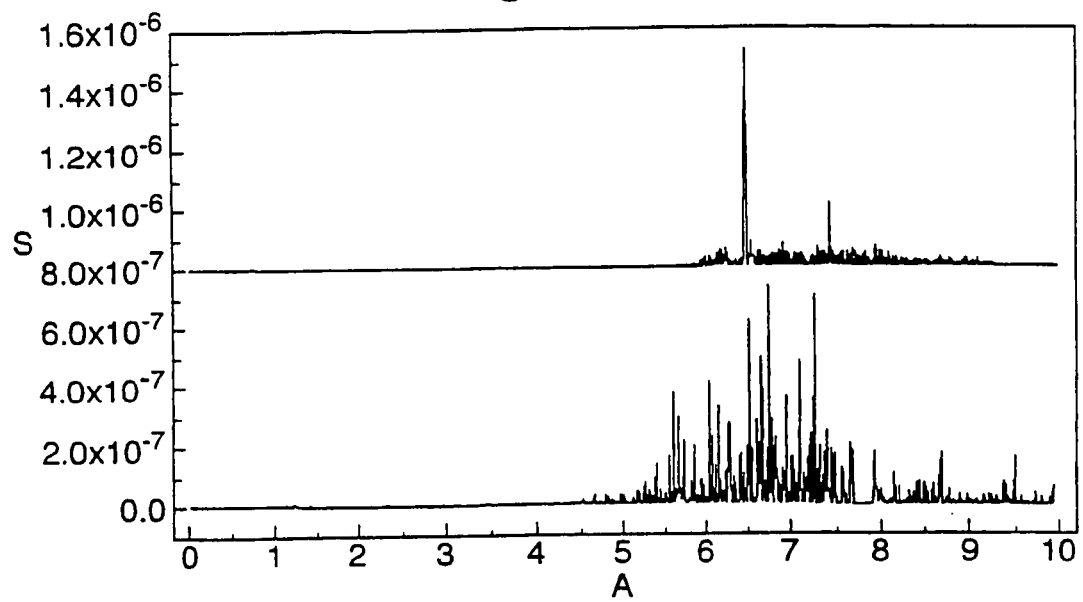
Figure 4D:
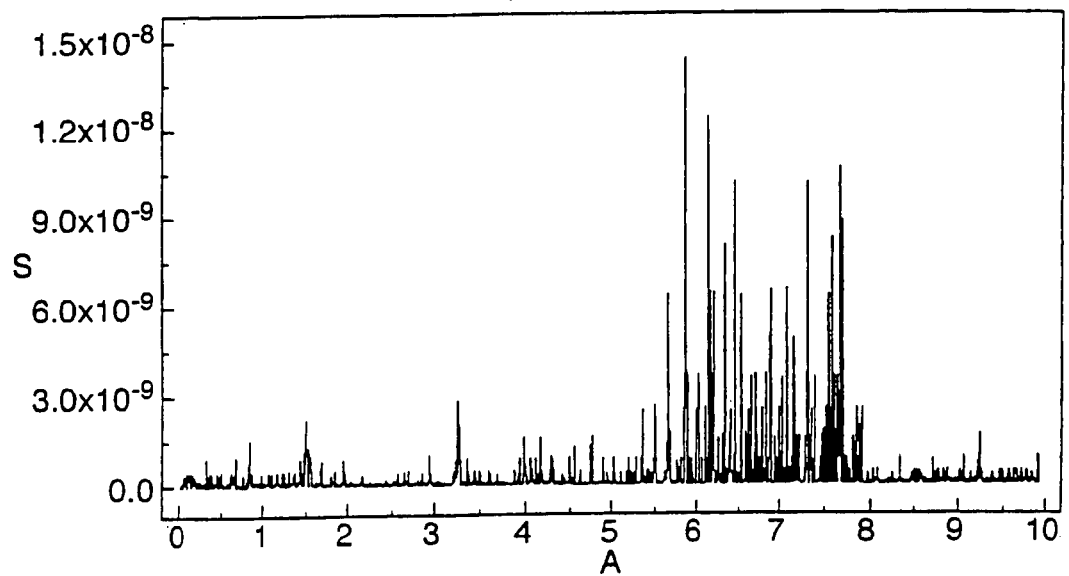

FIG. 4C shows the result of a control experiment performed in air with the maltose-binding phage when its binding site is blocked with maltose and the phage are then deposited on the QCM at the centre (top plot) or over the whole surface (bottom plot); this showed similar behaviour to the unmodified phage, confirming that the difference is due to these specific interactions. FIG. 4D shows the rupture force spectrum in water with only 1000 phage on the surface, and indicates that the rupture event is still detectable. There is a small shift in peak position due to smaller changes in the Q or quality factor of the QCM, as a result of the change in loading.

The data also suggest that it should be possible to separate the non-specifically bound phage from the maltose-binding phage by driving the QCM at a voltage above that for rupturing the bonds to the non-specifically bound phage but below that for the maltose-binding phage. This suggests an alternative way to screen phage libraries for binding, in which the binding affinity of the phage left on the surface is controlled by controlling the size of the applied voltage and the time for which it is applied, provided that the phage remain viable.

Figure 5A:
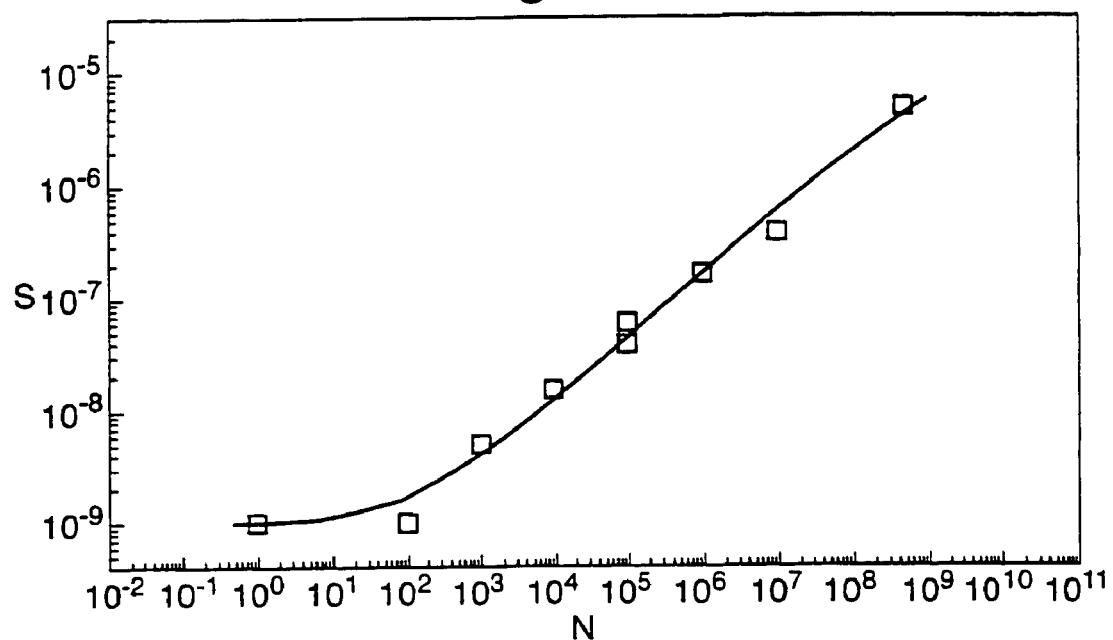
FIGS. 5A-B show plots of signal noise (S; arbitrary units) versus number of particles (N).
Figure 5B:
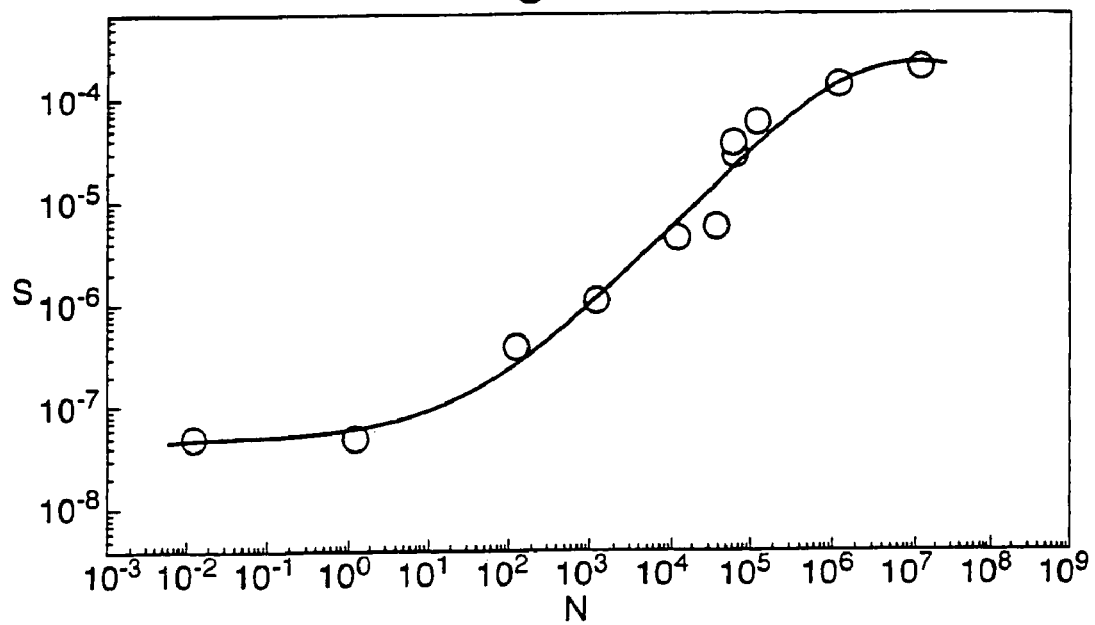

To determine the sensitivity of the method, a dilution experiment was performed, with the maltose-binding phage in water. FIG. 5A shows (for the most intense noise peaks near 9 V) that the power of the signal is linear with the number of phage over at least five orders of magnitude and that the presence of approximately 200 phage on the QCM can be detected with 99% probability. FIG. 5B shows a similar curve for the non-specific binding phage in air, indicating a detection sensitivity of 100 phage with 99% probability. The number of maltose-binding phage on the surface at low dilution was confirmed by direct imaging using an AFM.

This Example shows that the number of phage on the QCM surface may be detected. By contrast, using PCR, the number of copies of viral DNA is detected in solution. If it is assumed that all the virus particles in the solution sample will bind to the surface, which will occur if there is either a strong virus-surface interaction or the solution is allowed to evaporate leaving the viruses on the surface, then direct comparison of sensitivity is possible. The sensitivity of PCR is about 100 copies of viral DNA per mL which is comparable to detection sensitivity for the phage, by this Example (which is not optimised). The electronics may be improved, and there is scope to improve the sensitivity further, by possibly at least an order of magnitude. For example, in these experiments, the phage were deposited uniformly over the surface of the QCM. However both the amplitude and sensitivity of the QCM have a spatial dependence which means that the dominant signal comes from the centre of the QCM (as shown in FIG. 4C). This means fewer and hence more intense peaks could be recorded if the phage were only deposited in the centre of the QCM, resulting in an improvement in sensitivity.

This method can be straightforwardly extended to the detection of human viruses by the use of specific antibodies to the virus attached to the surface of the QCM. These antibodies form specific interactions between the virus attached to the surface of the QCM. These antibodies form specific interactions between the virus and the surface which can be broken at a particular surface acceleration. Non-specific adsorption by similar size or larger particles present in the sample will result in peaks at low voltage, as has now been shown, and this should not affect the analysis although adsorption by macromolecules onto the surface may reduce the number of antibodies available for binding to the virus. Most common viruses have a larger effective mass than the phage used in this Example although the number and strength of the specific interactions with the surface will be different. This means that the voltage required should be of a similar magnitude or smaller.

This Example shows that rupture force spectroscopy requires no amplification step, is quantitative, and has the potential to be immediate and low cost. This could lead to the rapid diagnosis of viral infection in many situations including patients in a clinical environment or plants and animals in agriculture.

EXAMPLE 4

This Example illustrates a virus binding assay. For this assay, quartz crystal microbalance chips were made from polished quartz plates, AT cut at an angle of 35° C. (HyQ, Cambridge, UK) and were coated in an Edwards vapour depositor with a 30 nm thick adhesion layer of chromium, then a 200 nm layer of gold as determined by calibrated electrical conductance. These chips were then immersed in a 1 mM solution of mercaptododecanoic acid in spectroscopic grade ethanol for 18 h, rinsed exhaustively with ethanol and then with water, and then blown dry under a stream of nitrogen. These chips were then immersed in a mixture of NHS (100 mM) and EDC (400 mM) for 20 min. They were rinsed exhaustively with water, then immersed for 1 h in a 50 µg/ml solution of mouse monoclonal IgG antibody raised against HSV I glycoprotein D in 10 mM PBS at pH 7.0. They were then rinsed with water and immersed for 10 min in a 1 M solution of ethanolamine at pH 8.5. They were then rinsed exhaustively with water and stored at 4° C. in 1 ml of PBS.

The number of viral particles/ml in a Ficoll-purified virus stock solution was determined using electron microscopy with an internal standard of latex spheres. Serial ten-fold dilutions of a HSV gD$^+$ stock solution at a concentration of $5 \times 10^{10}$ viral particles/ml were made in PBS (10 mM $Na_2HPO_4/NaH_2PO_4$, 2.7 mM KCl, 120 mM NaCl, pH 7.4) containing BSA (0.1 mg/ml) and stored at 4° C. The QCM chips were then mounted with solderless contacts in the instrument and either 1 μl or 40 μl of each of these dilutions was placed upon the chip surface coated with the anti-gD IgG antibody. After 40 min., the surface was washed thoroughly with water, then covered with 40 μl of PBS and the QCM scanned from 0-10 V.

Figure 6A:
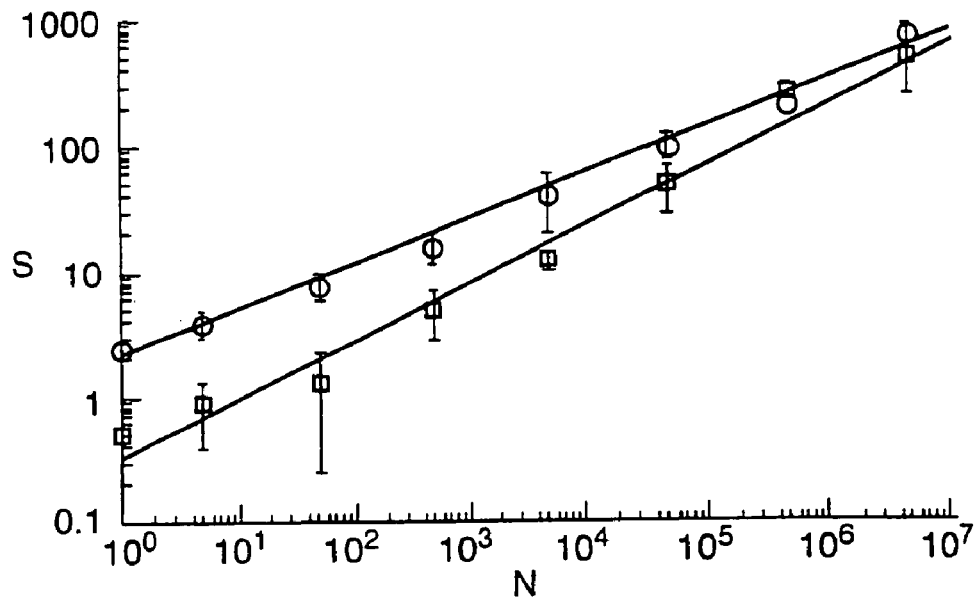
FIG. 6A shows plots of signal noise (S; arbitrary units) versus number of particles (N).
Figure 6B:
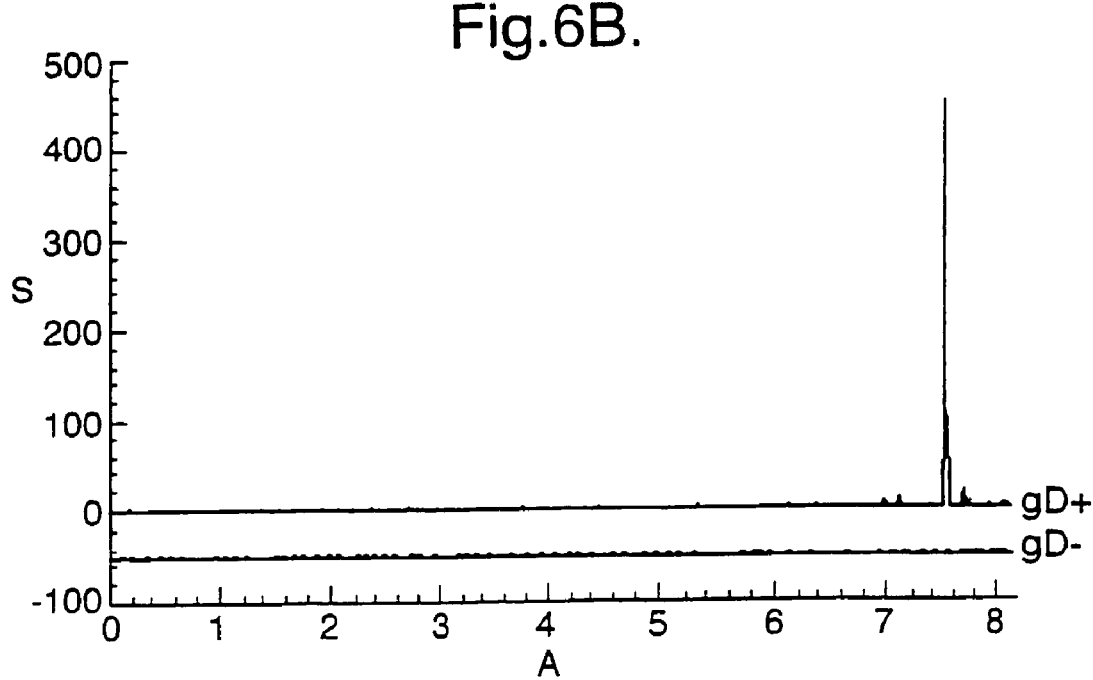
FIG. 6B shows (S; arbitrary units) versus amplitude (A; volts).

Results are shown in FIG. 6. FIG. 6A is a plot of signal (noise peak near 7.5 V) versus the number of gD$^+$ herpes simplex virus particles for the 1 μl (○) and 40 μl (□) samples; the line purity is good. FIG. 6B is a plot of noise versus amplitude for the gD$^+$ and gD$^-$ virus. The gD$^-$ virus, which has no specific interaction with the antibody on the surface, shows no peak; in contrast, the gD$^+$ virus shows a sharp peak near 7.5 V.

EXAMPLE 5

For this bacterial binding assay, QCM chips were prepared as in Example 4. *E. coli* and *S. aureus* (laboratory strains) were cultured in brain heart/0.5% yeast extract broth and incubated overnight at 37° C. A 1 ml sample of each culture was adjusted to a concentration of $10^{10}$ cfu/ml as determined by optical density, and centrifuged at 12,000 g for 2 min; the pellet was re-suspended in sterile PBS. 10 μl of the bacterial suspension was placed upon a QCM chip coated with an anti-*E. coli* IgG antibody in a manner similar to that described in Example 4 for the anti-HSV antibody. After 40 min., the surface was washed thoroughly with water, covered with 40 μl of PBS and the QCM then scanned from 0-10 V.

Figure 7:
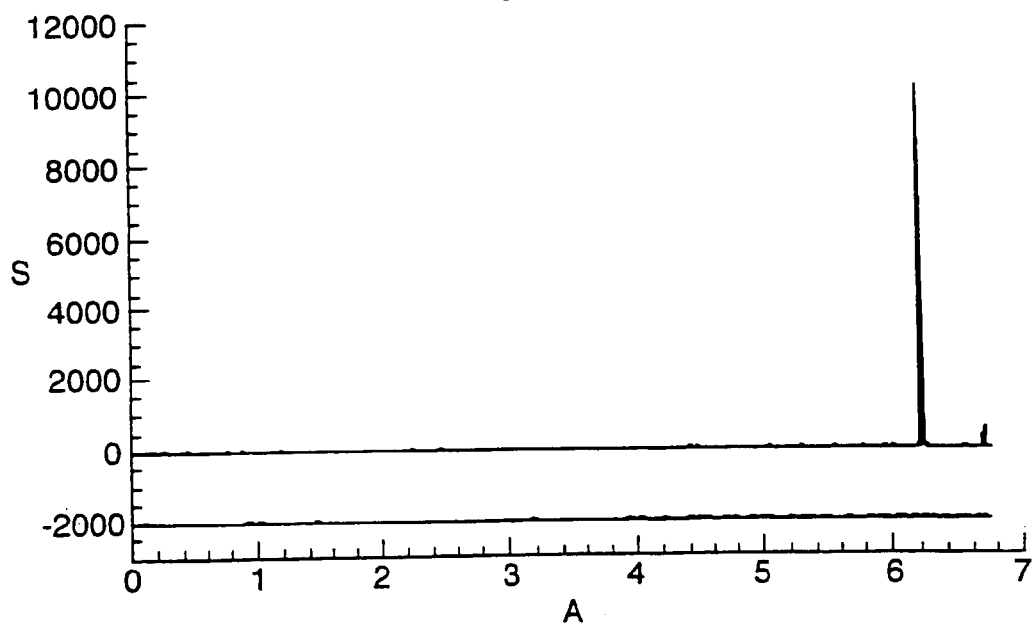
FIG. 7 shows plot of signal noise (S; arbitrary units) versus amplitude (A; volts).

Results are shown in FIG. 7. The noise/amplitude plot shows a sharp signal at about 6 V for *E. coli*, and none for *S. aureus*.

EXAMPLE 6

In this Example, a SAW device, as shown in FIG. 9, was used. In this case, a single instrument (HP8512a, Hewlett Packard) was used which combines an amplifier 1 and receiver and controller 5 in a single instrument. The instrument is set to a Continuous Wave and Power Sweep mode. The SAW device was the commercially available RF1171 from RF Monolitics, Inc. About 100,00 latex spheres, 1 μm in diameter were deposited on the surface of the SAW. The resulting spectrum is presented in FIG. 10. A number of peaks are observed, that are not present on the clean surface. This shows that a SAWS device can be used to detect the rupture event. The different peaks probably correspond to clusters of spheres on the surface of different sizes and hence the peaks are observed at different positions.

EXAMPLE 7

In this example, aggregates of a fragment of amyloid β protein, a disease-state protein which aggregates in cells during the course of Alzheimer's disease are detected by attachment to a quartz crystal prepared as above and coated with anti Ab 1-40 antibodies, which is then oscillated at a gradually increasing amplitude whilst measuring oscillations due to acoustic energy to detect rupture of amyloid aggregates from the oscillating surface.

Amyloid 62 protein fragment 1-40 (Aβ 1-40) was made up according to established procedures for formation of amyloid protein aggregates (Huang et al 1997, Journal of Biological Chemistry, 272 26464). As a control, the peptide in reverse, Aβ 40-1, was treated identically.

The Aβ 1-40 solution (500 mM) was visibly turbid, whereas Aβ 40-1 was visibly clear. This is a strong indication that the Aβ 1-40 solution comprised protein aggregates (Evans et al 1995, Proceedings of the National Academy of Sciences, 92, 763).

Figure 15:
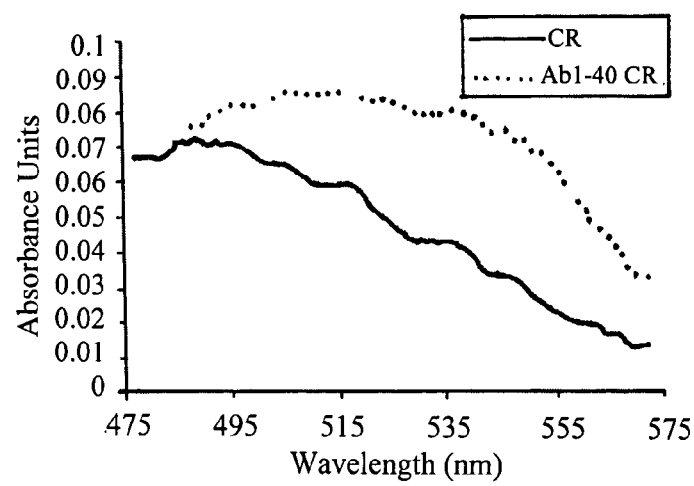
FIG. 15 is a measured absorbance spectrum of Congo red alone, and Congo red stained Ab 1-40.

In addition, the Congo red staining method, which specifically stains and quantifies b-sheet in Aβ 1-40, was used to determine the content of amyloid (Krebs M et al 2000, Journal of Molecular Biology, 300, 541; Goda S, 2000, Protein Science, 9, 369). The spectra for Congo red alone and Congo red stained Aβ 1-40 are shown in FIG. 15. From the spectra in FIG. 15 and the spectra of control protein Aβ 40-1, the concentration of amyloid forming β-sheet in the Aβ 1-40 sample could be determined. The concentration of β-sheet protein was found to be 336 mM and 7 mM for Aβ 1-40 and Aβ 40-1 respectively. The accuracy of these values is estimated to be no less than 14 mM from control experiments.

Thus, the Aβ 1-40 sample contained significant amounts of aggregate, in contrast to the control Aβ 40-1 sample.

Quartz crystals for use in these experiments were prepared as discussed above, with gold evaporated electrodes. Protein A/G was bound directly to the gold surface by physisorption. Protein A/G is subsequently used to immobilise and orientate antibody. The coating and functionality of this physisorbed protein A/G surface was confirmed using ellipsometry (for measuring protein thickness) and ELISA. 20 ml of 100 mg/ml Protein A/G in PBS was pipetted onto each gold electrode and incubated at 4° C. overnight, after which time the Quartz crystals were washed 3 times for 5 mins in PBS before being briefly rinsed in deionised H$_2$O and dried in a stream of nitrogen.

20 ml of mouse monoclonal anti-Aβ 1-40 or Bovine IgG (control QCM's) at 150 mg/ml was pipetted onto the gold electrodes protein A/G coated Quartz crystals and incubated overnight at 4° C. The Quartz crystals were then washed 3 times for 5 mins in PBS before being briefly rinsed in deionised H$_2$O and dried in a stream of nitrogen.

The Quartz crystals were mounted in static cell holders which allowed a reservoir of up to 50 ml of liquid to be held on top-of the Quartz crystal. 20 ml of 50 mM Aβ 1-40 in PBS or PBS alone (as a control) was added and incubated overnight at room temperature in a humid environment.

The potential applied to the Quartz crystal driver circuit was increased linearly from 0.2 to 10V. Acoustic signal measured during this potential sweep is illustrated, for the positive and two types of control, in FIG. 16.

Figure 16A:
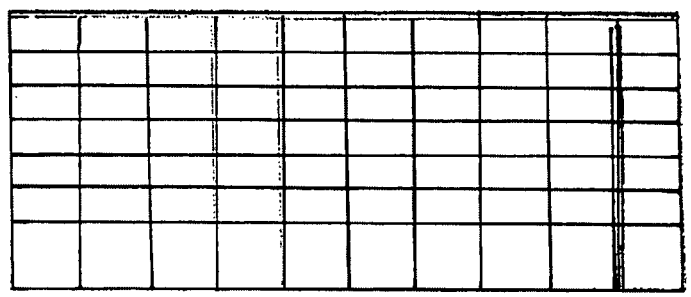
FIG. 16 is a graph of acoustic signal (y-axis) versus potential (x-axis) during a sweep of potential applied to a Quartz crystal driver circuit, where the crystal had been 16A) coated with anti Ab 1-40 monoclonal antibody, after which the crystal was exposed to Ab 1-40 aggregates; 6B) coated as before, but exposed only to PBS; and 6C) coated with non-specific bovine IgG and then exposed to Ab 1-40 aggregates.
Figure 16B:
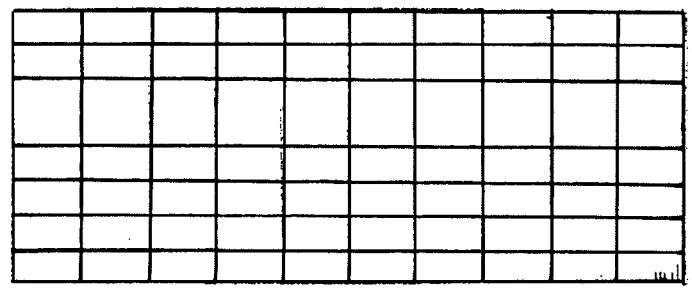
Figure 16C:
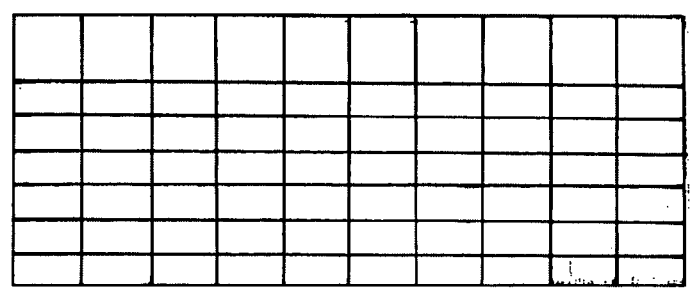

FIG. 16A is a graph of acoustic signal (y-axis) versus potential when Aβ 1-40 aggregates are incubated with an anti-Aβ 1-40 monoclonal antibody coated Quartz crystal. FIG. 16B is a corresponding graph where PBS only incubated with an anti Aβ 1-40 monoclonal antibody-coated QCM and FIG. 16C is a corresponding graph for Aβ 1-40 aggregates incubated with a non-specific bovine IgG-coated QCM. (Note that the Y axis scaling is different for the three scans, with full scales of 117, 14 and 11 for A, B and C, respectively.)

The heights of the largest peaks, within the window of 7 to 10 volts applied potential, were determined for each of the three samples. The resulting peak heights are plotted in FIG. 17 (data pooled from two separate experiments).

Figure 17:
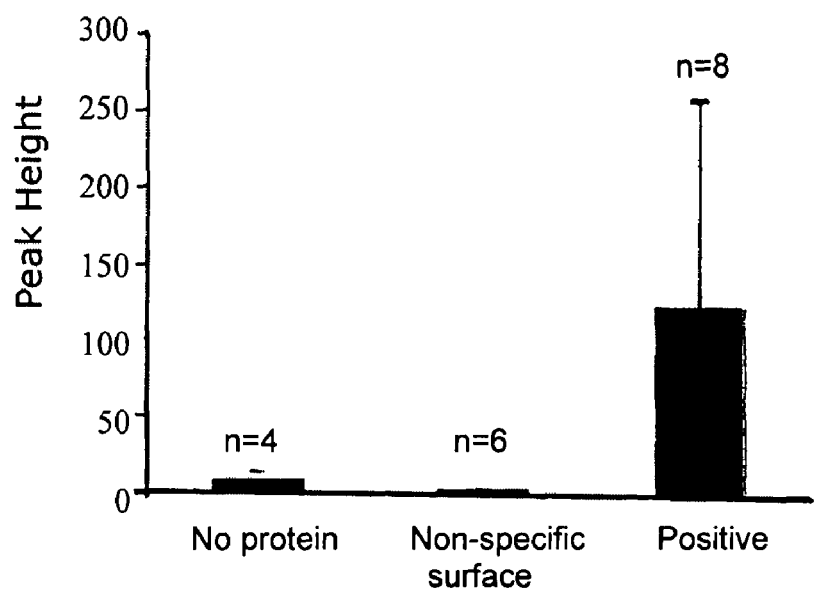
FIG. 17 is a bar chart of the heights of the peaks of graphs prepared as for FIG. 16, pooling the results of two separate experiments.

The positive shown in FIG. 17 is of the Aβ 1-40 aggregates incubated with an anti-Aβ 1-40 monoclonal antibody-coated Quartz crystal (as per FIG. 16A). A first control ("Non specific surface") comprised Aβ 1-40 aggregates incubated with a bovine IgG-coated Quartz crystal (as per FIG. 16B). A second control ("No protein") comprises PBS only incubated with an anti-Aβ 1-40 monoclonal antibody-coated Quartz crystal (as per FIG. 16C). Error bars represent 1 standard deviation.

Figure 18:
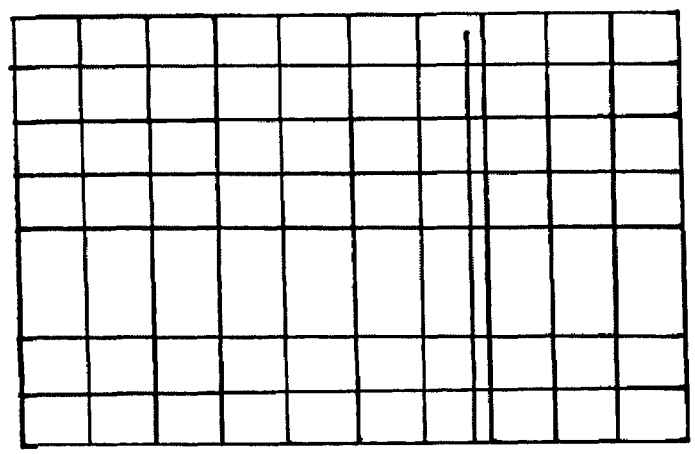
FIG. 18 is a graph of acoustic signal (y-axis) versus potential (x-axis) during a sweep of potential applied to a Quartz crystal driver circuit, where the crystal had been coated with anti Ab 1-40 monoclonal antibody, after which the crystal was exposed to Ab 1-40 aggregates, showing a clear single peak due to a rupture event.

In a further experiment, graphs of the detachment of amyloid aggregates of Aβ 1-40 from a coated quartz crystal surface were compared with control graphs where monomer Aβ 1-40 was used instead of amyloid aggregate as a control. 8 samples of Amyloid (Aβ 1-40 aggregate) and 5 monomer controls were analysed as above. FIG. 18 is a plot of detected acoustic signal vs. applied voltage in the region 0-9V. On the same scale, a typical control showed no signal across the range.

What is claimed is:

1. A method for separating first and second components in a fluid, which comprises the steps of:
   i. contacting the fluid with a surface having attached thereto a binding reagent to which said first and second components may bind; and
   ii. oscillating the surface at a first amplitude sufficient to rupture the bond between the binding reagent and the first component, but insufficient to rupture the bond between the binding reagent and the second component, thereby reducing or preventing the binding of the first component but not the second component
   wherein said first and second components are sufficiently different with respect to mass, size, nature of bond to the binding reagent, and/or geometric shape, to permit separation by said oscillation method.

2. The method according to claim 1, wherein the first component is more weakly bound to the binding reagent than the second component.

3. The method according to claim 1, wherein the first component has a lower effective mass than the second component.

4. The method according to claim 1, wherein the first component has a lower mass (molecular weight) than the second component.

5. The method according to claim 1, wherein the first component has a smaller size than the second component.

6. The method according to claim 1, wherein the first component has a different shape to the second component.

7. The method according to claim 1, wherein the second component is an aggregate of the first component.

8. The method according to claim 1, wherein the second component is an oligomer comprising the first component.

9. The method according to claim 1, wherein the or each component is a protein, antibody, antigen, enzyme, enzyme inhibitor or polynucleotide.

10. The method according to claim 1, wherein the or each component is a cell, bacterium, virus, prion or phage.

11. The method according to claim 1, wherein the second component is an oligomer of non-disease forming proteins.

12. The method according to claim 1, wherein the second component is an aggregate of disease-forming proteins.

13. The method according to claim 1, wherein the first component is a protein and the second component is a prion comprising said protein.

14. The method according to claim 1, wherein at least one component is immobilized to a microsphere.

15. The method according to claim 1, wherein the surface comprises a ligand which binds selectively to one component.

16. The method according to claim 1, wherein the oscillating is in the plane of the surface.

17. The method according to claim 1, which additionally comprises:
   iii. oscillating the surface at the second increased amplitude, sufficient to rupture the bond between the binding reagent and the second component, thereby releasing the second component.

18. The method according to claim 17, wherein the fluid comprises a third component that can bind to the surface, and the method optionally also comprises:
   iv. oscillating the surface at a third amplitude sufficient to rupture also the bond between the binding reagent and the third component.

19. The method according to claim 1 wherein the surface is formed on a transducer which comprises a piezoelectric material.

20. The method according to claim 1 wherein the amplitude of the oscillation of the surface is increased, whilst the frequency of the oscillations is held constant or approximately constant.

* * * * *